(12) United States Patent
Borzacchiello et al.

(10) Patent No.: US 12,226,549 B2
(45) Date of Patent: Feb. 18, 2025

(54) SYNERGISTICALLY COOPERATIVE COMPOSITIONS USEFUL FOR SOFT TISSUE AUGMENTATION, DRUG DELIVERY AND RELATED FIELDS

(71) Applicant: ALTERGON S.A., Lugano (CH)

(72) Inventors: Assunta Borzacchiello, Naples (IT); Maurizio Pagliuca, Lugano (CH); Nicola Solimando, Lugano (CH); Luigi Nicolais, Ercolano (IT)

(73) Assignee: ALTERGON S.A., Lugano (CH)

( * ) Notice: Subject to any disclaimer, the term of this patent is extended or adjusted under 35 U.S.C. 154(b) by 829 days.

(21) Appl. No.: 17/264,134

(22) PCT Filed: Jul. 24, 2019

(86) PCT No.: PCT/EP2019/069892
§ 371 (c)(1),
(2) Date: Jan. 28, 2021

(87) PCT Pub. No.: WO2020/025415
PCT Pub. Date: Feb. 6, 2020

(65) Prior Publication Data
US 2022/0118155 A1    Apr. 21, 2022

(30) Foreign Application Priority Data

Jul. 31, 2018   (IT) .................. 102018000007683

(51) Int. Cl.
*A61L 27/26* (2006.01)
*A61K 31/192* (2006.01)
(Continued)

(52) U.S. Cl.
CPC ............ *A61L 27/26* (2013.01); *A61K 31/192* (2013.01); *A61K 31/196* (2013.01);
(Continued)

(58) Field of Classification Search
CPC .......................... A61L 27/26; A61L 2300/236
(Continued)

(56) References Cited

U.S. PATENT DOCUMENTS 8,642,067 B2    2/2014  Trogden et al.
8,846,094 B2 *  9/2014  Lyons et al. ............. A61K 9/14
                        (Continued)

FOREIGN PATENT DOCUMENTS

CN    104349780 A      2/2015
DE    102014203152 A1  8/2015
(Continued)

OTHER PUBLICATIONS

Abu-Fayyad A, et al. PEGylated γ-tocotrienol isomer of vitamin E: Synthesis, characterization, in vitro cytotoxicity, and oral bioavailability. European Journal of Pharmaceutics and Biopharmaceutics. Oct. 1, 2015;96:185-95 (Year: 2015).*

(Continued)

*Primary Examiner* — Jeffrey S Lundgren
*Assistant Examiner* — Heather Dahlin
(74) *Attorney, Agent, or Firm* — LUCAS & MERCANTI, LLP

(57) ABSTRACT

The present invention relates to compositions based on: (a) a glycosaminoglycan or mixtures thereof; (b) one or more tocopherols, tocotrienols and mixtures thereof; and (c) a selected stabilizer. The composition is a solution, with the agents not chemically bound with each other. The component (a) can be hyaluronic acid (HA) or a salt thereof; the component (b) can be a polyether clathrate a cyclodextrin, or a combination of a fatty acid with an emulsifier; the component (c) can be α-tocopherols, β-tocopherols, γ-tocopherols, δ-tocopherols; α-tocotrienols, β-tocotrienols, γ-tocotrienols, δ-tocotrienols. Preferably component (c) is vitamin E. The agents strongly cooperate to provide enhanced and (Continued)

more stable viscoelastic properties, resulting in a product with higher resistance to thermal treatments like e.g. heat-sterilization, autoclaving, etc. The present compositions, optionally loaded with pharmaceutically and/or cosmetically active agents, are advantageously used in medical or cosmetic methods.

14 Claims, 18 Drawing Sheets

(51) Int. Cl.
| | |
|---|---|
| A61K 31/196 | (2006.01) |
| A61K 31/407 | (2006.01) |
| A61K 31/421 | (2006.01) |
| A61K 31/4365 | (2006.01) |
| A61K 31/4706 | (2006.01) |
| A61K 31/496 | (2006.01) |
| A61K 31/5415 | (2006.01) |
| A61K 31/60 | (2006.01) |
| A61K 31/616 | (2006.01) |
| A61K 47/22 | (2006.01) |
| A61K 47/36 | (2006.01) |
| A61K 47/40 | (2006.01) |

(52) U.S. Cl.
CPC .......... *A61K 31/407* (2013.01); *A61K 31/421* (2013.01); *A61K 31/4365* (2013.01); *A61K 31/4706* (2013.01); *A61K 31/496* (2013.01); *A61K 31/5415* (2013.01); *A61K 31/60* (2013.01); *A61K 31/616* (2013.01); *A61K 47/22* (2013.01); *A61K 47/36* (2013.01); *A61K 47/40* (2013.01); *A61L 2300/21* (2013.01); *A61L 2300/216* (2013.01); *A61L 2300/232* (2013.01); *A61L 2300/236* (2013.01); *A61L 2300/41* (2013.01)

(58) Field of Classification Search
USPC .......................................................... 514/567
See application file for complete search history.

(56) References Cited

U.S. PATENT DOCUMENTS

| | | | |
|---|---|---|---|
| 8,946,192 B2* | 2/2015 | Gousse et al. | ....... A61K 31/715 |
| 9,138,405 B2 | 9/2015 | Gavard Molliard et al. | |
| 9,370,575 B2* | 6/2016 | Lin | ........................ A61K 47/36 |
| 2003/0008817 A1 | 1/2003 | Sander et al. | |
| 2004/0076680 A1 | 4/2004 | Soltes et al. | |
| 2005/0101582 A1 | 5/2005 | Lyons et al. | |
| 2005/0181017 A1 | 8/2005 | Hughes et al. | |
| 2006/0140988 A1 | 6/2006 | Chen et al. | |
| 2006/0141049 A1 | 6/2006 | Lyons et al. | |
| 2007/0224278 A1 | 9/2007 | Lyons et al. | |
| 2008/0268051 A1 | 10/2008 | Hughes et al. | |
| 2009/0143348 A1 | 6/2009 | Tezel et al. | |
| 2014/0038917 A1 | 2/2014 | Gavard Molliard et al. | |
| 2015/0051168 A1 | 2/2015 | Kim et al. | |
| 2015/0151005 A1 | 6/2015 | Bouchemal | |
| 2016/0129134 A1* | 5/2016 | Boiteau | .................. A61K 47/48 |

FOREIGN PATENT DOCUMENTS

| | | | | |
|---|---|---|---|---|
| EP | 1967186 A1 * | 9/2008 | ........... | A61K 31/135 |
| WO | 2009089845 A1 | 7/2009 | | |
| WO | 2013076162 A1 | 5/2013 | | |
| WO | 2014005822 A1 | 1/2014 | | |
| WO | 2015181365 A1 | 12/2015 | | |

OTHER PUBLICATIONS

International Search Report and Written Opinion for Corresponding International Application No. PCT/EP2019/069892 (13 Pages) (Dec. 16, 2019).

* cited by examiner

A

C

D

A

B

D

A

SYNERGISTICALLY COOPERATIVE COMPOSITIONS USEFUL FOR SOFT TISSUE AUGMENTATION, DRUG DELIVERY AND RELATED FIELDS

CROSS-REFERENCE TO RELATED APPLICATIONS

This application is a 371 of PCT/EP2019/069892, filed Jul. 24, 2019, which claims the benefit of Italian Patent Application No. 102018000007683, filed Jul. 31, 2018.

FIELD OF THE INVENTION

The present invention concerns the field of products and compositions with viscoelastic properties optionally loaded with active ingredients as drug delivery systems, useful in the medical, surgical and dermo-esthetic area, as well as methods for enhancing and stabilizing such viscoelastic properties.

BACKGROUND OF THE INVENTION

Synovial joints are the most numerous joints, particularly in the limbs. In these joints, bones are united via a cavity filled with a liquid both viscous and elastic called synovial fluid. Synovial fluid is responsible for the operation and protection of joints. In the synovial fluid, there is an elevated concentration of high molecular weight glycosaminoglycans like hyaluronic acid, chondroitin sulfate etc. In particular, hyaluronic acid (HA) serves as shock absorber and provides necessary lubrication for the joints and, it reduces friction of the moving bones and thus diminishing wear. Under inflammatory conditions, such as osteoarthritis or rheumatoid arthritis, high MW HA is degraded by reactive oxygen species (ROS), which reduce its viscosity and its lubricant and shock absorbing properties, leading to deteriorated joint movement and pain so that the natural cushioning between joints cartilage wears away. When this happens, the bones of the joints rub more closely against one another with less of the shock-absorbing benefits of cartilage. The rubbing results in pain, swelling, stiffness, decreased ability to move and, sometimes, the formation of bone spurs. While knee osteoarthritis is often a progressive and irreversible degenerative process, functional improvement and pain control are reasonable treatment goals. Intra-articular injection of hyaluronic acid or its derivative (viscosupplementation products) is one of the most used therapies for the treatment of knee osteoarthritis, its objective being to restore the elastic and viscous properties of the synovial fluid (SF). The beneficial improvements in SF viscoelastic properties and joint functions derive from both the intrinsic viscoelastic properties of HA and its potential stimulatory effect on the synthesis of high-molecular weight (HMW) HA by synoviocytes. Moreover, to stimulate the production of healthy HA and facilitate the homeostasis in the joint region, oral administration of anti-inflammatory drugs is often necessary in combination, or as an alternative to HA viscosupplementation. However, the prolonged use of such drugs causes important systemic adverse effects. One of the major issues concerning the use of viscosupplementation agents is the reduction of number of injections by increasing the residence time of HA. To this aim chemical modification or intra and inter-molecular chemical crosslinking are performed to stabilize the HA network and improve the viscoelastic properties. These methods often can impair HA biological properties.

Concerning the skin, the largest organ of the human body, HA plays a series of important functions: it can immobilize water in tissue and thereby change dermal volume and compressibility; act as a scavenger of free radicals generated by the ultraviolet rays from sunlight; influence cell proliferation, differentiation, and tissue repair. Changes in HA observed with ageing, wound healing, and degenerative diseases further highlight its importance in skin. For instance, HA concentration in the dermis decreases with the age promoting the formation of wrinkles. Solutions or hydrogels of hyaluronic acid, in recent years, raised big interest in the area of cosmetic surgery for the rejuvenation of the dermis.

Hyaluronic acid (HA) or hyaluronan is a naturally occurring linear polysaccharide that is widely used for biomedical applications. In the last years increased attention has been paid on the use of HA in the biomaterial field thanks to its significant characteristics such as hydrophilicity, viscoelasticity, and biocompatibility, resorb ability and ability to be chemically modified. HA is a glycosaminoglycan composed of repeating disaccharide units of D-glucuronic acid and N-acetyl-D-glucosamine linked by β-1-3 and β-1-4 glycosidic bonds. HA is a primary component of the extra-cellular matrix of the mammalian connective tissues, an important structural element in the skin and it is present in high concentration in the synovial joint fluids, vitreous humor of the eyes, hyaline cartilage, disc nucleus and umbilical cord. HA plays a major role in several functions in vivo such as lubrification of arthritis joints, viscoelastic properties of soft tissue and it plays a pivotal role in many biological functions such as cell motility, cell matrix adhesion and cell organization. HA interacts with specific cells receptors such as CD44 and RHAMM. HA molecules in solution behave as expanded random coils that can overlap each other and interact through secondary bonds resulting in a network displaying viscoelastic properties. This network can be further stabilized by guest molecules that can synergistically interact with HA, improving viscoelastic properties and stability of HA solutions.

Cyclodextrins are cyclic oligosaccharides able to form inclusion complexes with a variety of drugs and are known to improve solubility of hydrophobic drugs, such as Diclofenac (DF) which are used as an anti-inflammatory drug, and protect against physicochemical and enzymatic degradation. Cyclodextrins (CD) are naturally available cyclic oligosaccharides and have good biocompatibility and biodegradation. The CDs and its derivatives (α, β and γ-CD) are natural cyclic oligosaccharides and consist of (α-1,4)-linked α-D-glucopyranose unit. α-, β-, and γ-CDs are made up of 6, 7, and 8 glucose units, respectively. The CDs are shaped like a truncated cone having an interior hydrophobic cavity, which is surrounded by a hydrophilic outer surface. The CDs have been extensively used to form inclusion complexes with a variety of lipophilic drug molecules, aromatic compounds, ions, polymers, or any suitable molecules due to their low toxicity, excellent biocompatibility and non-immunogenicity. During the formation of an inclusion complex, the drug (guest) molecules are partially or completely entrapped inside its hydrophobic cavity with no covalent bonding. Most of the studies have been focused on the formation of inclusion complexes for cancer therapy.

Among the fatty acids, it is the omega-3 polyunsaturated fatty acids (PUFA) which possess immunomodulatory activities, they have a double bond (C=C) at the third carbon atom from the end of the carbon chain. The three types of omega-3 fatty acids involved in human physiology are α-linolenic acid (ALA), eicosapentaenoic acid (EPA), and docosahexaenoic acid (DHA). Omega-3 polyunsaturated fatty acids (PUFAs) play a crucial role in brain function, as well as normal growth and development. They have also become popular because they may reduce the risk of heart disease. omega-3 fatty acids reduce inflammation and may help lower risk of chronic diseases such as heart disease, cancer, and arthritis.

Vitamin E (VE) is a general term referring to a group of lipid-soluble bioactive compounds including tocopherols (α-, β-, γ-, and δ-tocopherol) and tocotrienols (α-, β-, γ-, and δ-tocotrienol). Vitamin E and its derivatives are potent antioxidants, as they scavenge lipid peroxyl radicals by donating hydrogen from the phenolic group on the chromanol ring. Because they possess similar phenolic moieties, all vitamin E forms are considered to have potent antioxidant activities.

Various glycosaminoglycan-based products are described in the art, generally for used as supports (aids) for viscosupplementation.

For example, the U.S. Pat. No. 9,138,405B2 discloses methods of producing HA formulation in the form of gel with optionally one or more other naturally occurring polysaccharides, and one or more polyols including sorbitol, mannitol or a mixture thereof to use the formulation for intra-articular injection in the treatment of joint degeneration.

The U.S. Pat. No. 9,138,405B2 describes a composition comprising hyaluronic acid, a gold compound and a polymer, wherein the gold compound inhibits degradation of hyaluronic acid. The invention relates to enhancing the duration and activity of implanted hyaluronic acid materials.

The patent application US20090143348A1 discloses gel compositions and methods for sustained delivery of drugs, the composition including at least one target solute grafting onto a HA via covalent bond. The composition is useful for cosmetic and medical applications, and products and related methods for using and making the same.

The patent application US20030008817A1 application describes compositions capable of restoring normal mechanical properties to collagenous tissue damaged through natural aging process, which contain HA and thiazolium (or salts thereof, or combinations thereof). The formulation can increase lubrication within a joint, and nourish said tissue with structural and support materials damaged or destroyed a result of the aging process.

Compositions for therapeutic or cosmetic use comprising a high molecular weight hyaluronic acid and one or more active agents are widely disclosed. See e.g. U.S. patent application Ser. Nos. 11/039,192; 11/695,527; 11/742,350; 10/966,764; 11/354,415, and; Ser. No. 11/741,366.

The patent application US20140038917A1 discloses sterile and injectable aqueous formulations for administration in the infra-articular space of an intra-articular joint of a subject, in the form of a gel comprising HA and a polyol wherein the ratio between the concentrations of polyol and acid hyaluronic, or one of its salts, is comprised between about 0.155 to 14, and wherein said sterile and injectable aqueous formulation is adapted for the administration in one single dose injection and has a zero-shear rate viscosity η0 equal or higher than 15 Pa·s.

The patent application US20060140988A1 discloses a composition comprising HA with a surfactant, wherein the surfactant is a polyoxyethylene sorbitan-containing composition, a block copolymer of propylene oxide and ethylene oxide, a block copolymer derived from the addition of ethylene oxide and propylene oxide to ethylenediamine, polyethylene glycol, or polyethylene oxide. The invention relates to methods and depot emulsion compositions for delivery of viscosupplements.

The patent application US20040076680 describes the preparation of HA derivatives in which the HA is chemically modified via chemical cross-linking thereof with a polymer different from HA, e.g. a cyclodextrin, and their use as medicines.

US 20150151005A1 application describes modification of HA with fatty acid in combination with α-CD. The hydrophobized polysaccharide being obtained by grafting of alkyl chains derived from fatty acids, by an acylation reaction.

Critical for compositions and solutions used in the field of viscosupplementation is their capacity to mimic the viscoelastic behavior of the synovial fluid, so as to work as proper replacement/integration thereof. The target viscoelastic properties can be obtained by suitably operating on the parameters of the chosen biopolymer (e.g. molecular weight, molecular weight distribution, concentration in solution, use of salts or derivatives etc.); however reaching the target viscoelastic profile may require high amounts of biopolymer and consequently high production costs. Moreover, a challenge to these products is maintaining the desired viscoelastic behavior over time, especially during manufacturing which often involves subjecting the biopolymer solution to high-impact sterilization treatments at elevated temperatures and pressures (autoclaving): these treatments are notoriously detrimental to the biopolymer stability, causing an undesired variation in viscoelastic properties, hardly adjustable at such late stage of manufacturing.

The need is thus felt for new, improved biopolymer products, useful for viscosupplementation and related fields, which overcome one or more of the limitations discussed above.

SUMMARY

It was now found that compositions based on: (a) a glycosaminoglycan or mixtures thereof, (b) one or more tocopherols or tocotrienols and mixtures thereof and (c) a selected stabilizer, give rise to a cooperative system (complex) in which the three entities (a)-(c) synergistically cooperate with one another, without being engaged in formal chemical binding with each other, to achieve an increased viscoelastic profile and an elevated degree of protection of the same, obtaining a product suitable to withstand high-impact treatments like e.g. thermal sterilization. The composition of the present invention is provided in aqueous solution form, with the agents (a), (b), (c) being present within specific concentration ranges. The glycosaminoglycan can be e.g. hyaluronic acid (HA) or a salt thereof; the stabilizer can be a polyether clathrate, e.g. a cyclodextrin, or a combination of a fatty acid with an emulsifier; the tocopherols can be chosen among α-, β-, γ-, and δ-tocopherols; the tocotrienols can be chosen among α-, β-, γ-, and δ-tocotrienols, and mixtures thereof; a preferred mixture of tocopherols and tocotrienols used in the invention is Vitamin E. The present compositions, optionally loaded as drug delivery systems with one or more pharmaceutically and/or cosmetically active agents, are useful in the dermo-cosmetic, esthetic, orthopedic medical and surgical fields for soft tissue augmentation, viscosupplementation, dermal-filler and for regenerative treatment.

DESCRIPTION OF THE FIGURES

(FIG. 1A, 1B) or 37° C. (FIG. 1C, D).

(FIG. 2A, 2B) or 37° C. (FIG. 2C, 2D).

(FIG. 3A, 3B) or 37° C. (FIG. 3C, 3D).

(FIG. 4A, 4B) or 37° C. (FIG. 4C, 4D).

DETAILED DESCRIPTION OF THE INVENTION

Figure 1:
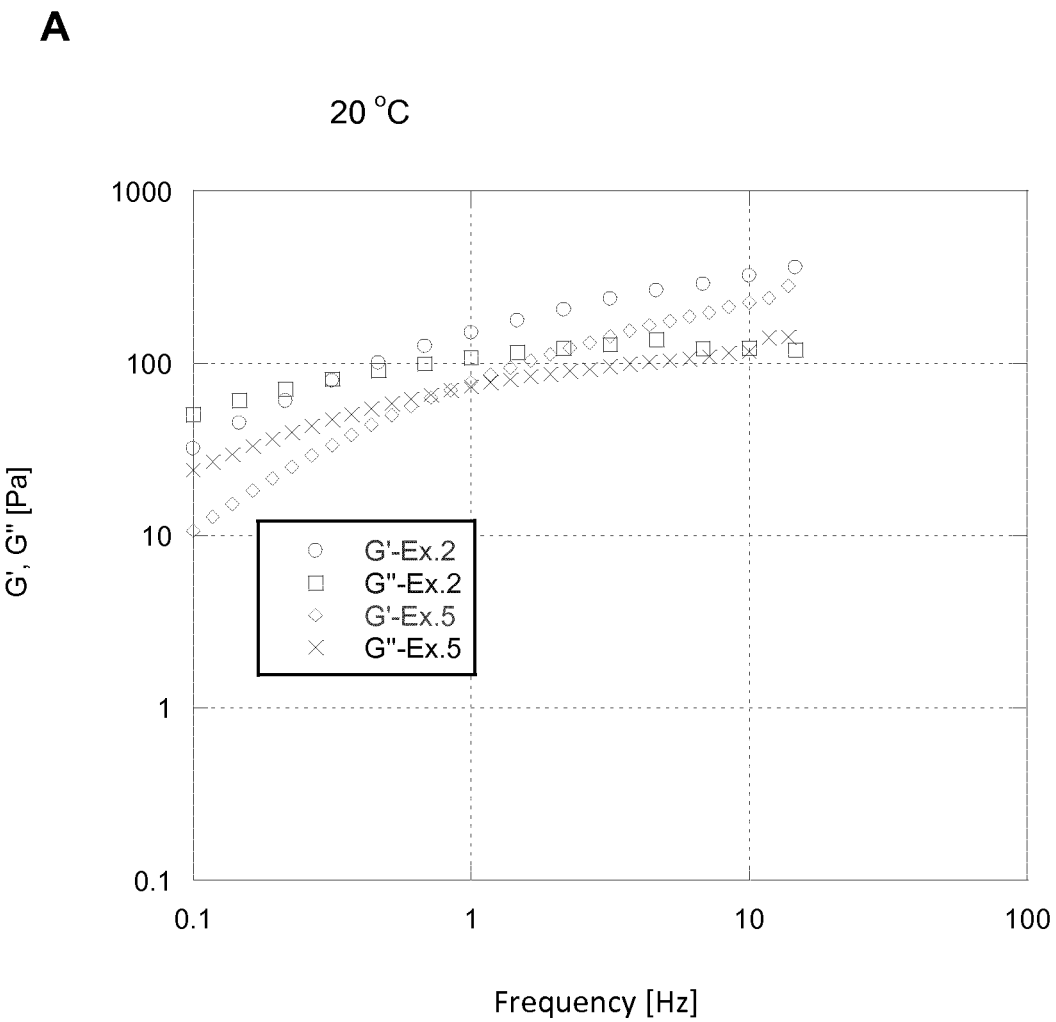
FIG. 1 compares the mechanical spectra of Example 2 (invention) and 5 (reference), recorded prior/after performing the autoclaving (AC) cycle: the spectra are recorded at 20° C.
Figure 1:
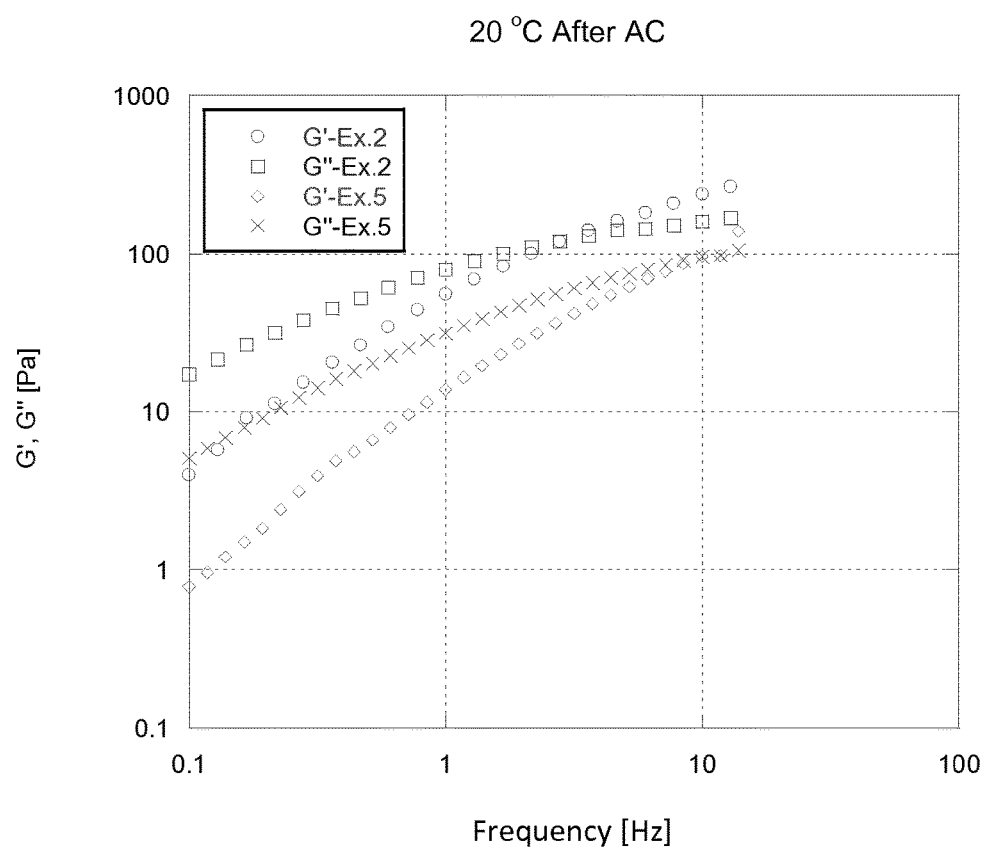
Figure 1:
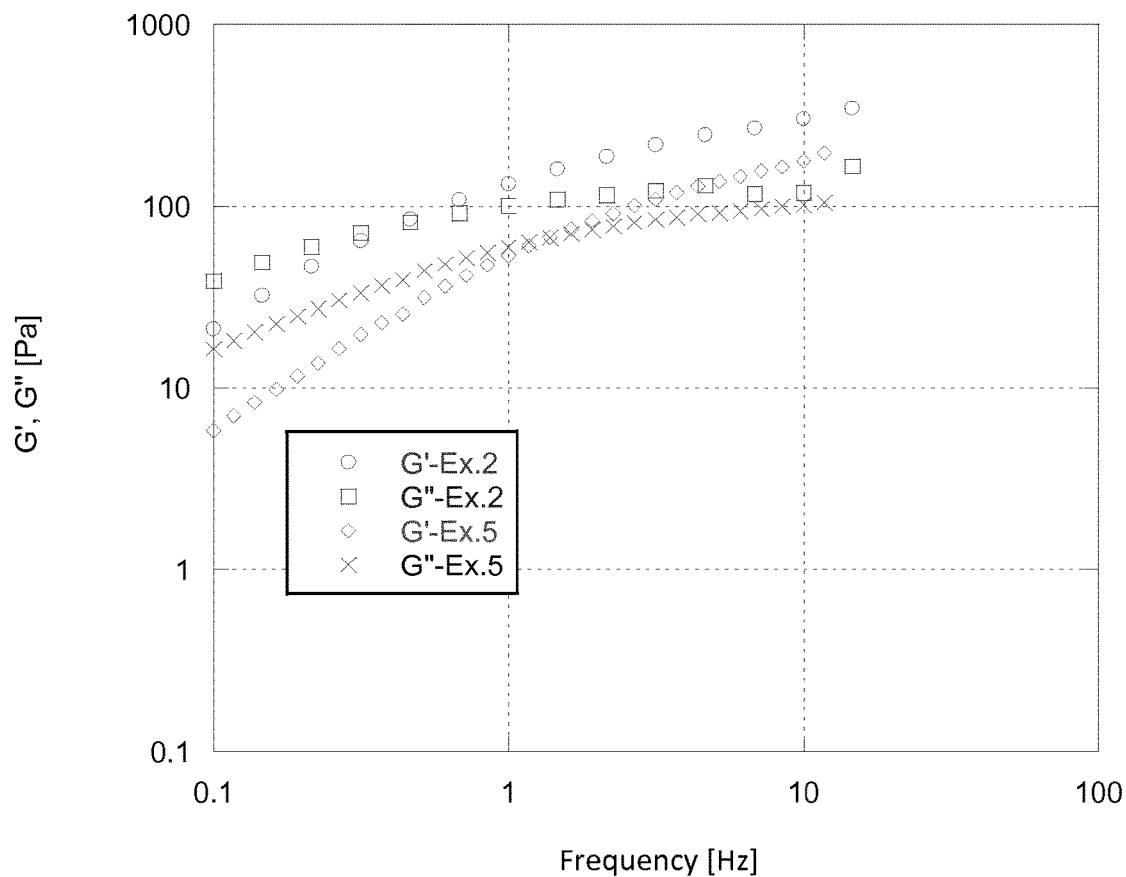
Figure 1:
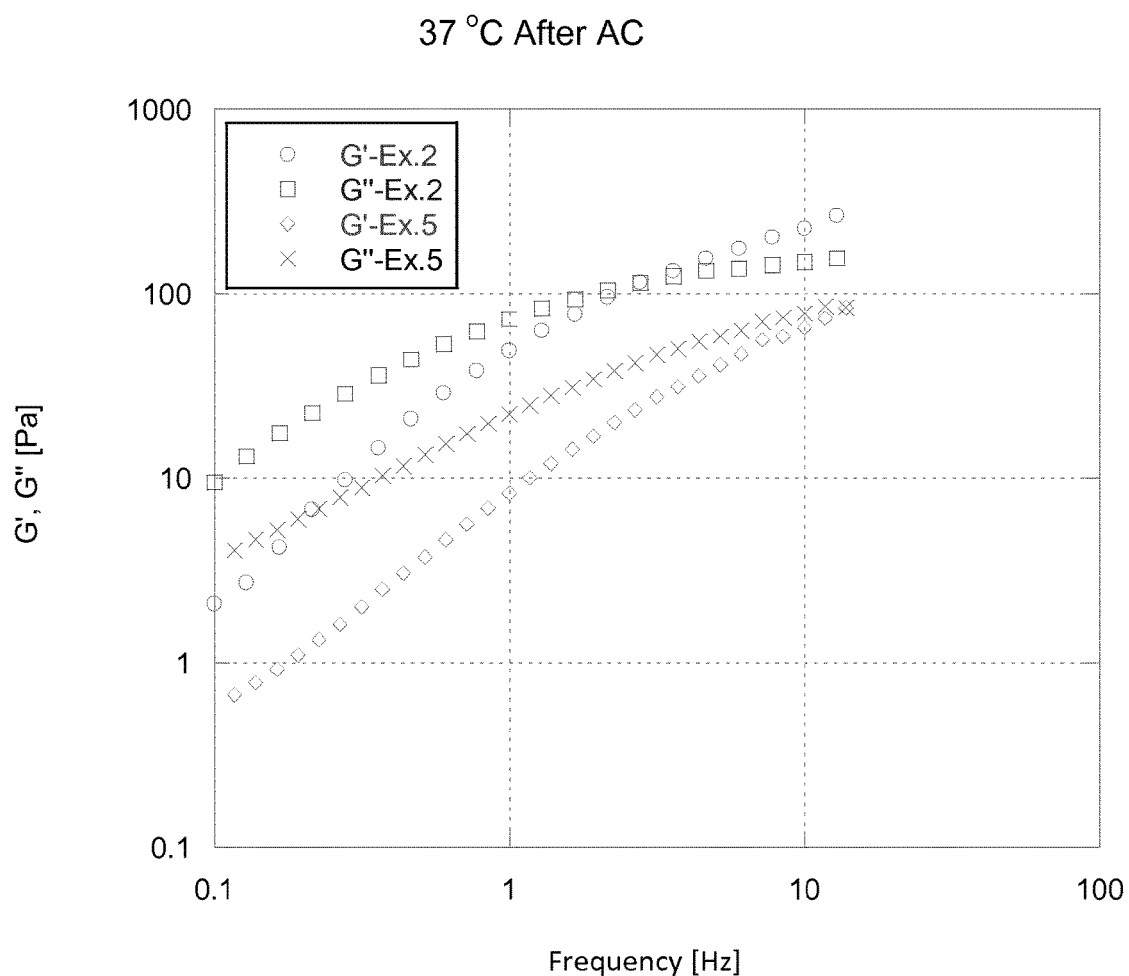

The term "synergistically cooperative", used herein in respect of a composition or product means a composition or product wherein its components interact with one another in such a way that one component enhances the viscoelastic performance of a product made by other components; in the present invention, this property is obtained by formulating the composition or product in accordance with the present claims.

The term "aqueous", referred to a solution, indicates a solution containing water for more than 50%, preferably more than 85%, more preferably more than 95% of its weight, in association with a water-miscible solvent, e.g ethanol, n-propanol, i-propanol, etc.; most preferably the term "aqueous" means water as the sole solvent; the aqueous solution can also be a buffered aqueous solution, for example a phosphate buffer solution (PBS), e.g. buffered at a physiologically compatible pH. From the physical point of view, the term "solution" is broadly used herein to indicate a homogeneous liquid system whose components are therein dissolved and/or finely dispersed. e.g. emulsified.

The term "composition" used herein, means the result of a physical mixing of its components (glycosaminoglycan, vitamin E and stabilizer) in which each of them maintains its individuality as a single molecule. Consequently, the term "composition" excludes products characterized by a formal chemical binding among the above components, such as realized by covalent binding; the term "composition" remains yet compatible with products in which said components are in free state or they are coordinated via electrostatic forces, e.g. hydrogen bonds, hydrophobic interactions, Van der Waals interactions, solvation forces, etc.; they may also be engaged via other forms of physical binding e.g. by incorporation, inclusion, emulsion, etc. The same conditions apply also to pharmaceutically or cosmetically active ingredients (optionally) present in the compositions.

The present compositions are also described herein as "complexes", wherein this term includes coordination complexes and extends to functional complexes, i.e. any system in which the single components, retaining their individual molecular character, cooperate synergistically to improve the viscoelastic properties of the composition.

The term "glycosaminoglycan" means herein, in agreement with the technical literature, a polysaccharide containing a repeating disaccharide unit, said repeating unit containing an amino sugar (e.g. N-acetylglucosamine or N-acetylgalactosamine) along with an uronic sugar (e.g. glucuronic acid or iduronic acid) or galactose. Glycosaminoglycans are highly polar and attract water. They are useful to the body as a lubricant or as a shock absorber. Examples of glycosaminoglycans useful for the purpose of the present invention are hyaluronic acid and salts thereof, as well as chondroitin sulfate, chondroitin salts (e.g. sodium chondroitin), dermatan sulfate, heparan sulfate, etc. Mixtures of one or more of glycosaminoglycans can also be used in the present invention; particularly preferred are mixtures of hyaluronic acid with one or more glycosaminoglycans different from hyaluronic acid, in particular chondroitin sulfate. The glycosaminoglycan is used in the present solutions at a weight concentration of 0.01 to 25% by weight of the solution, preferably 0.01 to 10%, more preferably 0.1 to 10%; when mixtures of two or more glycosaminoglycans are used, the above intervals of concentration are meant to be referred to the total weight of glycosaminoglycans by weight of the solution.

Hyaluronic acid is a preferred glycosaminoglycan for use in the present invention. The term "hyaluronic acid" means herein, in agreement with common general knowledge, a glycosaminoglycan composed of repeating disaccharide units of N-acetylglucosamine (GlcNAc) and glucuronic acid (GlcUA) linked together by alternating beta-1,4 and beta-1,3 glycosidic bonds. Hyaluronic acid is also known as hyaluronan, hyaluronate, or HA. The terms hyaluronan, hyaluronic acid and HA are used interchangeably herein. Hyaluronic acid can be used as such or in a salt form (hyaluronate) and has average molecular weight preferably comprised between 40 kDa to 4000 kDa; a particularly preferred product for use in the invention is the Ultrapure sodium hyaluronate produced in accordance with the patent publication WO2014/005822 herein incorporated by reference. The HA is used in the invention within the concentration ranges referred above for glycosaminoglycans. Other preferred glycosaminoglycans are chondroitin sulfate and chondroitin salts (e.g. sodium chondroitin), dermatan sulfate, heparan sulfate and derivatives thereof.

"Vitamin E" refers, as well known in the art, to a group of compounds that include both tocopherols and tocotrienols (in particular, $\alpha$-, $\beta$-, $\gamma$-, or $\delta$-tocopherols and $\alpha$-, $\beta$-, $\gamma$-, or $\delta$-tocotrienols). The term "Vitamin E" means herein any of these compounds taken alone or any of its mixtures, irrespective of whether such compounds or mixtures occur in nature; the term "Vitamin E" also includes any possible salts and derivatives of the above compounds, e.g. Vitamin E esters, such as tocopherol acetate. Vitamin E is well-known as a peroxyl radical scavenger, disabling the production of damaging free radicals in tissues, by reacting with them to form a tocopheryl radical, which will then be reduced by a hydrogen donor and thus return to its reduced state. As it is fat-soluble, it is incorporated into cell membranes, which protects them from oxidative damage. In the present invention, the Vitamin E is used at a weight concentration from 0.0001 to 15%, preferably 0.1 to 15%, more preferably 0.1 to 10%, by weight of the solution. When mixtures of tocopherols and/or tocotrienols are used, the above intervals of concentration are meant to be referred to the total weight of said tocopherols and/or tocotrienols by weight of the solution.

The stabilizer is used in the present invention in a weight concentration range from 0.01 to 25% preferably 0.01 to 10%, more preferably 0.1 to 10% by weight of the solution. The term "stabilizer" refers herein in general to selected products capable to enhance/stabilize the viscoelastic performance of a physical mixture of glycosaminoglycan and vitamin E. Stabilizers according to the present invention are chosen from polyether clathrates, e.g. a cyclodextrin, or a mixture of fatty acid with an emulsifier.

"Polyether clathrates" are herein defined as structures comprising one or more macrocyclic rings (i.e. containing at least 12 atoms) said ring comprising, separated from each other, two or more oxygen heteroatoms (i.e. the ring comprises at least two ether bonds). From the functional point of view, as known in the art, clathrates form a molecular cage capable of hosting foreign molecules, compatibly with the mutual dimensions. Preferred examples of polyether clathrates for use in the present invention are cyclodextrins. Cyclodextrins are hydrophobic inside and hydrophilic outside, they can form complexes with hydrophobic compounds; they can enhance the solubility and bioavailability of such compounds. Cyclodextrins are able to form host-guest complexes with hydrophobic molecules given the nature imparted by their structure. This is of high interest for pharmaceutical as well as dietary supplement applications in which hydrophobic compounds shall be delivered. Examples of cyclodextrins are $\alpha$-, $\beta$-, or $\gamma$-cyclodextrin (in which the macrocyclic ring as described above contains, respectively 30, 35 or 40 atoms). Particularly preferred for use in the present invention are derivatized cyclodextrin, such as propyl-$\beta$-cyclodextrin, sulfobutyl-$\beta$-cyclodextrin, sulfobutyl ether 4-$\beta$-cyclodextrin, hydroxypropyl-$\beta$-cyclodextrin, hydroxypropyl-$\gamma$-cyclodextrin; mixtures of cyclodextrins are also contemplated by the invention. Other examples of polyether clathrates, different from cyclodextrins, are crown ethers, for example, 12-crown-4, 15-crown-5, 18-crown-6, dibenzo-18-crown-6 ether.

Another stabilizer which can be used in the present invention is a combination of fatty acid with an emulsifier: these two ingredients are regarded herein as one component ("stabilizer"), even when they are separately added to the composition. In all these cases, the above given ranges of concentration for the stabilizer (0.01 to 25% preferably 0.01 to 15%, more preferably 0.1 to 10%) are meant to refer to the total weight of fatty acid and emulsifier, by weight of the solution; the whole of fatty acid and emulsifier, generally contains from 0.0995 to 9.5% by weight of fatty acid, the remainder being the emulsifier. The combination of fatty acid and emulsifiers can be prepared apart and added to the other components of the cooperative composition or, in alternative, the fatty acid and the emulsifier can be added separately thereto; in both cases the fatty acid and the emulsifier are able to interact and form an emulsion, whereby the fatty acid is homogeneously dispersed within the present solutions.

Fatty acids can be organic, monobasic acids derived from hydrocarbons by the equivalent of oxidation of a methyl group to an alcohol, aldehyde, and then acid. Fatty acids can be saturated and unsaturated. Preferred fatty acids are $\omega$-3 fatty acids. The term "fatty acids" used herein includes, for example, lipoic acid, oleic acid, linoleic acid, linolenic acid, $\alpha$-linolenic acid, eicosapentaenoic acid, docosahexaenoic acid or other omega-3-fatty acids; the term "fatty acids" also extends to molecules which are derivatized with fatty acids, such as triglycerides, phospholipids etc. Suitable non-ionic emulsifier include poly(oxyethylene)-poly(oxypropylene) block copolymers, commercially known as poloxamer and pluronic; polysorbates, such as Tween 20 or Tween 80. Amphoteric surfactants include quaternized imidazole derivatives.

The present compositions may optionally include one or more pharmaceutically and/or cosmetically active ingredients, where the term "active" identifies compounds or entities that alter, inhibit, activate or otherwise affect biological or chemical events obtaining, respectively, a pharmaceutical- or cosmetic effect. Preferably, the active ingredient is a drug for human or animal use, with no limitations as to the pharmacologic class. Preferred pharmaceutically active agents used in the invention are anti-inflammatory drugs: examples thereof are e.g. salicylic acid, aspirin, mefenamic acid, tolfenamic acid, flufenamic acid, diclofenac, diclofenac, sulindac, fenbufen, indometacin, acemetacin, amfenac, etodolac, felbinac, ibuprofen, flurbiprofen, ketoprofen, naproxen, pranoprofen, fenoprofen, tiaprofenic acid, oxaprozin, loxoprofen, alminoprofen, zaltoprofen, piroxicam, tenoxicam, lornoxicam, meloxicam, tiaramide, tolmetin, diflunisal, acetaminophen, floctafenine, tinoridine, actarit, pharmaceutically acceptable salts thereof (for example diclofenac sodium), and mixtures thereof. When present, the pharmaceutically or cosmetically active agent is at a weight concentration preferably comprised from 0.0001 to 10% by weight of the solution; it may be present in free form or in electrostatic interaction with one or more of the main components of the composition (glycosaminoglycan, vitamin E and stabilizer). When more pharmaceutically and/or cosmetically active agents are present, the above concentration range is meant to be referred to the total sum of such agents.

Further excipients can be optionally present in the compositions, depending on the specific type of formulation considered and its final use. Among the excipients, there can be mentioned: preservatives, viscosity adjusting agents (thickening or fluidifying agents), emulsifiers (if not already present as fatty acid/emulsifier mixture), chelating agents, buffering agents, tonicity adjusting agents, co-solvents, etc. further optional agents present in the compositions are antioxidants such as ascorbic acid, melatonin, vitamin C, proteins (e.g., serum hyaluronidase inhibitors), etc.

A further object of the present invention is a process to prepare a composition as above described. In its general scope, the process comprises forming an aqueous solution of: (a) a glycosaminoglycan or mixtures thereof, (b) a stabilizer as herein defined, and (c) one or more tocopherols, tocotrienols and mixtures thereof, wherein the glycosaminoglycan is present at a concentration of 0.01 to 25%; the stabilizer is present at a concentration of 0.01 to 25% by weight; the tocopherols, tocotrienols and mixtures thereof are present at a concentration of 0.0001 to 10% by weight of the solution. In a more detailed embodiment, the above process is performed by adding into a suitable mixer: the stabilizer, the glycosaminoglycan and the tocopherols/tocotrienols; when the stabilizer is a lipid with emulsifier, they can be added separately or in premixed form; the aqueous component can be added at any time, at once or preferably stepwise, during the above described procedure; typically the aqueous component is added (at least in part) together with the first component being introduced in the container and the remainder (if any) is added in one or more steps during the rest of the process. All the above operations are suitably performed under agitation, which can be continued after the last addition for a time sufficient to obtain a single homogeneous phase, typically 2-10 hours; the whole process can be conveniently performed at ambient temperature (20-25° C.).

The compositions of the invention may be finally sterilized to obtain a product of pharmaceutical/cosmetic grade. All sterilization procedure can be used, e.g. ultrafiltration, dry heat, wet heat, $\gamma$-radiation, etc. Advantageously, the above referred components cooperate synergistically in protecting the resulting solution, in particular its viscoelastic profile, from thermal degradation: the solutions are thus treatable in autoclave procedures (as examples a typical autoclaving cycle involves treatment at 121° C., at a pressure of about 1 atm for 20 minutes or equivalent validated combination to obtain a sterile product) or by other thermal methods, with lesser influence on their final viscoelastic properties, compared to glycosaminoglycan solutions currently used for viscosupplementation; the increased thermal resistance can be verified by standard means, in particular in terms of preservation of elastic modulus G' and the viscous modulus G" in a frequency range from 0.01 to 10 Hz.

A further set of embodiments of the present invention is described by the following clauses 1-17.

1. A synergistically cooperative composition, in aqueous solution form, comprising: (a) glycosaminoglycan or mixtures thereof at a weight concentration of 0.01 to 25%, (b) cyclodextrin at a weight concentration of 0.01 to 25%, (c) a lipid with emulsifier a weight concentration of 0.0001 to 15%, by weight of the solution, wherein said components (a), (b) and (c) are not engaged in formal chemical binding with each other.
2. Composition according to clause 1, wherein the glycosaminoglycan is selected from hyaluronic acid or salt thereof, chondroitin sulfate, sodium chondroitin, dermatan sulfate or heparan sulfate.
3. Composition according to clauses 1-2, wherein the hyaluronic acid in form of two or more fractions thereof with different average molecular weights, each comprised between 40 to 4000 kDa.
4. Composition according to clauses 1-3 wherein the hyaluronic acid salt is selected from sodium, potassium, ammonium, calcium, magnesium, zinc and cobalt salts and mixtures thereof.
5. Composition according to clauses 1-4, wherein the lipid comprises one or more of lipoic acid, oleic acid, linoleic acid, linolenic acid, α-linolenic acid, eicosapentaenoic acid, docosahexaenoic acid or other omega-3-fatty acids, triglycerides and phospholipids.
6. Composition according to clauses 1-5, wherein the emulsifier is selected from phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; polyoxyethylene-9-lauryl ether; sorbitan trioleate (Span 85) glycocholate; sorbitan monolaurate (Span 20); polysorbate 20 (Tween-20); polysorbate 60 (Tween-60); polysorbate 65 (Tween-65); polysorbate 80 (Tween-80); polysorbate 85 (Tween-85); poloxomers or pluronics; sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol) 5000-phosphatidylethanolamine; poly(ethylene glycol) 400-monostearate; phospholipids; synthetic and/or natural detergents having high surfactant properties; deoxycholates; cyclodextrins; chaotropic salts; ion pairing agents; and mixtures thereof.
7. Composition according to clauses 1-6, wherein the tocopherol is chosen from an α-, β-, γ- or δ-tocopherol and mixtures thereof.
8. Composition according to clauses 1-7, wherein the tocotrienol is chosen from an α-, β-, γ- and δ-tocotrienol and mixtures thereof.
9. Composition according to clauses 1-8, further comprising a pharmaceutically- or cosmetically active agent.
10. Compositions according to clause 9, wherein the pharmaceutically active agent includes one or more non-steroidal anti-inflammatory drugs.
11. Composition according to clause 10, wherein the anti-inflammatory drug is selected from salicylic acid, aspirin, mefenamic acid, tolfenamic acid, flufenamic acid, diclofenac, sulindac, fenbufen, indometacin, acemetacin, amfenac, etodolac, felbinac, ibuprofen, flurbiprofen, ketoprofen, naproxen, pranoprofen, fenoprofen, tiaprofenic acid, oxaprozin, loxoprofen, alminoprofen, zaltoprofen, piroxicam, tenoxicam, lornoxicam, meloxicam, tiaramide, tolmetin, diflunisal, acetaminophen, floctafenine, tinoridine, actarit, pharmaceutically acceptable salts thereof and mixtures thereof, in concentration of 0.0001 to 10% by weight of the solution.
12. Composition according to clause 11, wherein the antiinflammatory drug is diclofenac sodium.
13. A stabilized cooperative complex in accordance with clauses 1-12.
14. A process of preparing a composition or complex according to clauses 1-13, comprising forming an aqueous solution of a glycosaminoglycan or mixtures thereof at a weight concentration of 0.01 to 25%, a fatty acid and emulsifier at overall weight concentration of 0.01 to 25% by weight and one or more tocopherols or tocotrienols and mixtures thereof at a weight concentration of 0.0001 to 15%, by weight of the solution.
15. The composition or complex according to clauses 1-13, for use in therapy.
16. The composition or complex according to clauses 1-13, for use in a medical method of treatment selected from: dermo-cosmetic, esthetic, soft tissue augmentation, viscosupplementation, dermal-filling, regenerative treatments and drug delivery applications.
17. Use of the composition or complex according to clauses 1-13, in a cosmetic method of treatment selected from: dermo-cosmetic, esthetic, soft tissue augmentation, viscosupplementation, dermal-filling, regenerative treatments.

The invention is further described in non-limitative manner by the following examples.

EXAMPLES

1. Formulations and Preparation

The following Table shows the composition of the Formulation Examples 1 to 5.

TABLE 1

Composition of Formulation Examples 1 to 5.

| Composition | Example 1 | Example 2 | Example 3 w/w % | Example 4 | Example 5 |
|---|---|---|---|---|---|
| HA | 2 | 2 | 2 | 2 | 2 |
| FA (omega 3 mixtures) | 1 | 1 | — | — | — |
| Pluronic | 0.02 | 0.02 | — | — | — |
| CD | — | — | 2 | 2 | — |
| VE | — | 2 | — | 2 | 2 |

HA = hyaluronic acid;
FA = fatty acid;
CD = cyclodextrin;
VE = Vitamin E

1.1. Examples 1 (Reference) and 2 (Invention)

Solutions according to Examples 1 and 2 were obtained by the following procedure:
  Suitable emulsifier was weighed into an appropriate container and then diluted in PBS.
  FA was weighed and added to the previous solution.
  HA according to the formulation Examples, and Vitamin E if present, were added to the previous mixture at room temperature.
  Finally, the previous mixture was diluted by PBS, maintaining stirring for at least 3 to 8 hours.
  The product resulting from described procedure is homogeneous with one phase.

1.2. Examples 3 (Reference) and 4 (Invention)

Solutions according to Examples 3 and 4 were obtained by the following procedure:
  CD was weighed into an appropriate container and then diluted in Phosphate Buffer Solution (PBS).
  HA according to the formulation Examples, and Vitamin E if present, were added to the previous solution at room temperature.
  Finally, the previous mixture was diluted by PBS, maintaining stirring for at least 3 to 8 hours.
  The product resulting from described procedure is homogeneous with one phase.

1.3. Example 5 (Reference)

The solution according to Example 5 was obtained by the following procedure:
  HA according to the formulation Example, and Vit E, were added to PBS, maintaining stirring for at least 3 to 8 hours.
  The product resulting from described procedure is homogeneous with one phase.

2. Assessment of Viscoelastic Properties

Viscoelastic properties measurements were carried out through a strain controlled rotational rheometer (Mars III, HAAKE Rheometer, Waltham, MA USA), using a parallel plate geometry at 20 and 37° C. The frequency was in the range from 0.01 to 10 Hz. In order to identify the linear viscoelastic response range of the materials, preliminary strain sweep tests were performed on the samples, at the oscillation frequency of 1 Hz. The tests were repeated at least three times on each sample.

The dependence of the elastic modulus G' and the viscous modulus G" as function of frequency, the so called "mechanical spectra" are reported in the FIGS. 1-4. In particular:

FIG. 1 compares the mechanical spectra of Example 2 (invention) and 5 (reference), prior/after performing the autoclaving (AC) cycle: the spectra are recorded at 20° C. (FIG. 1A, 1B) or 37° C. (FIG. 1C, D).

Figure 2:
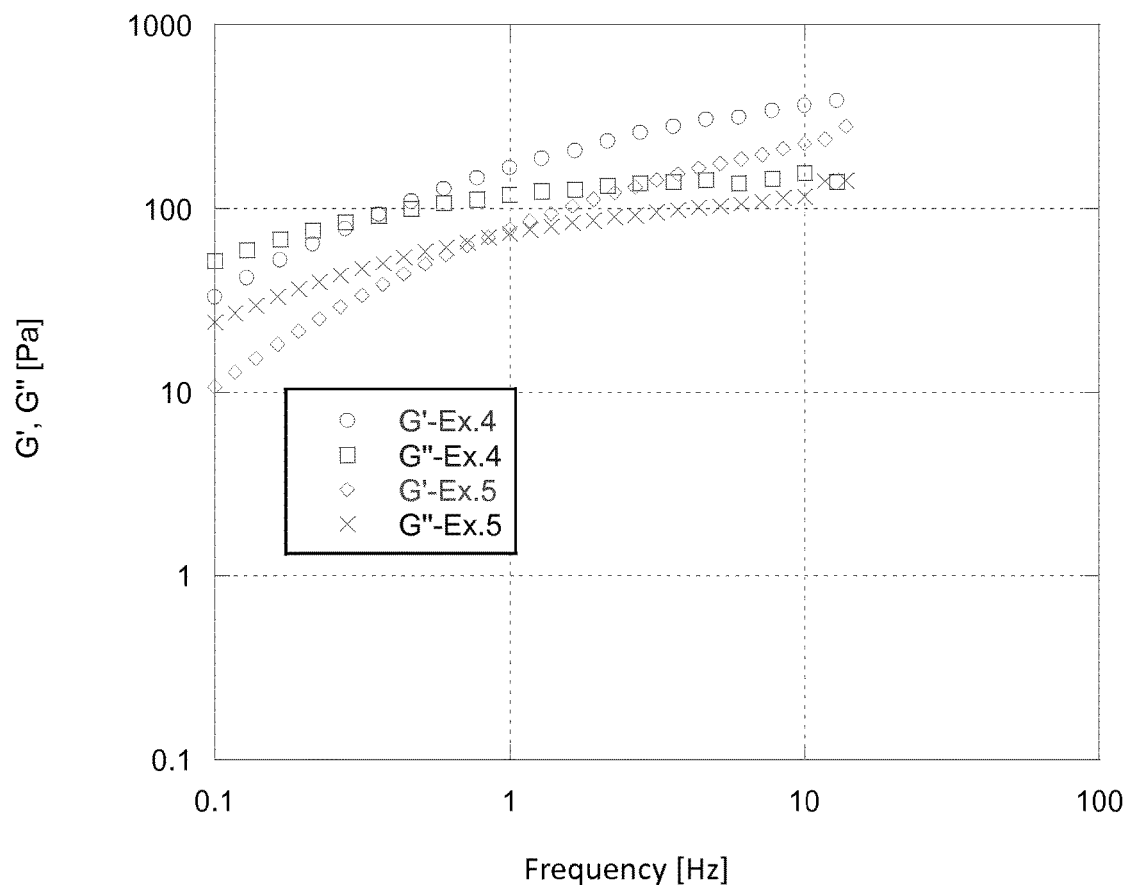
FIG. 2 compares the mechanical spectra of Example 4 (invention) and 5 (reference), recorded prior/after performing the autoclaving (AC) cycle: the spectra are recorded at 20° C.
Figure 2:
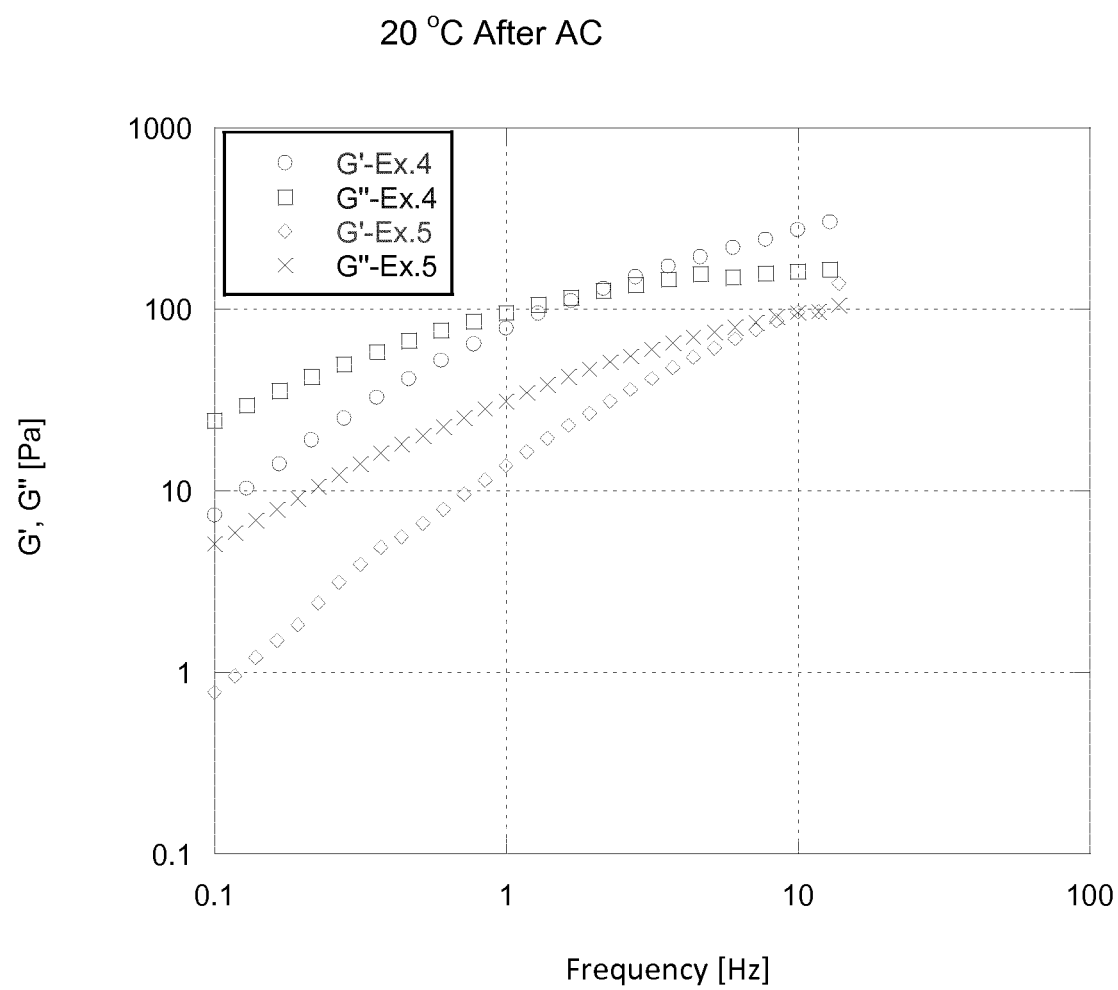
Figure 2:
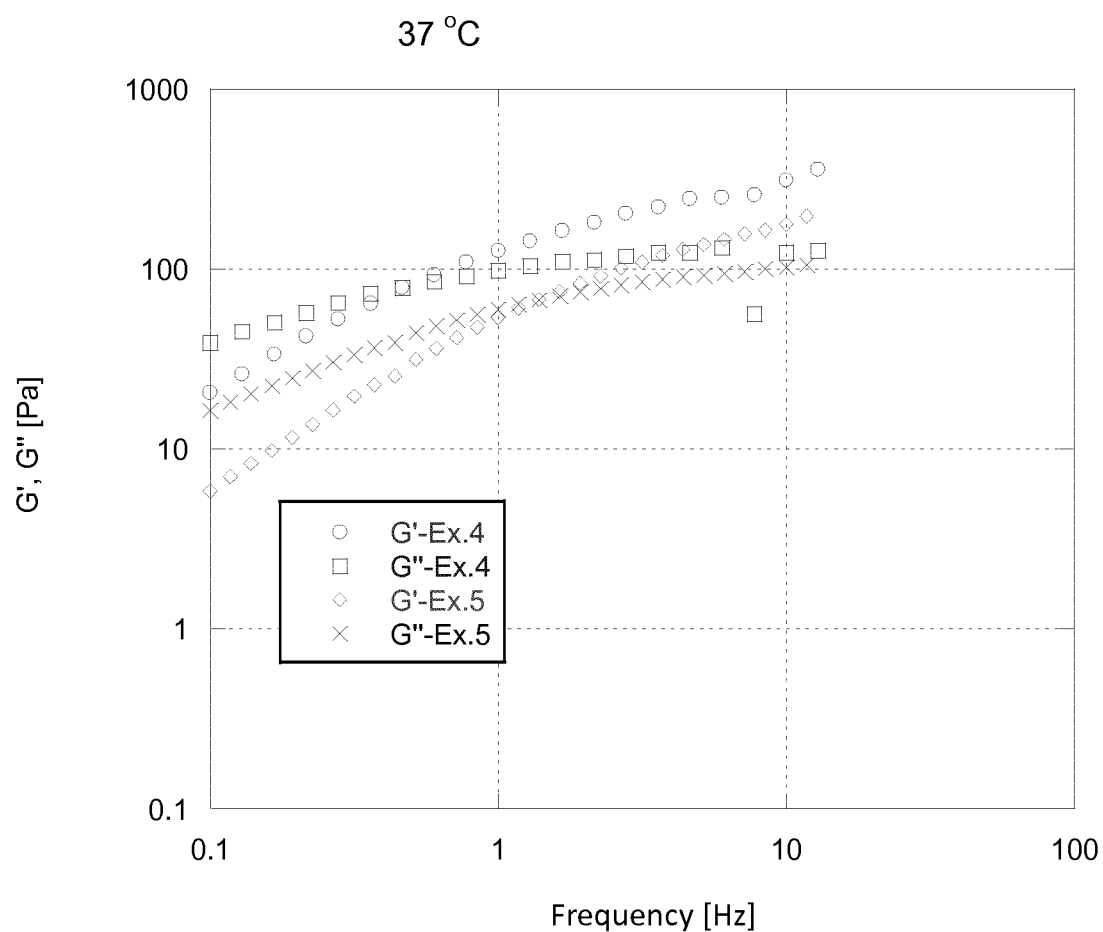
Figure 2:
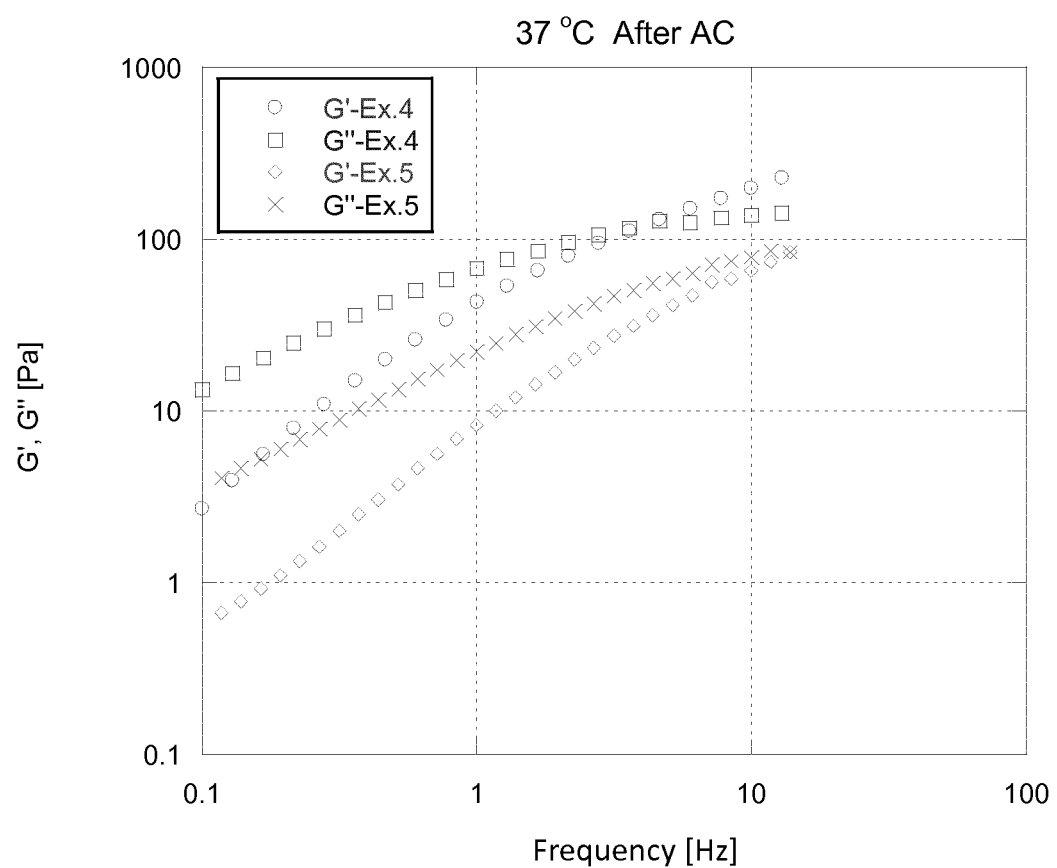

FIG. 2 compares the mechanical spectra of Example 4 (invention) and 5 (reference), prior/after performing the autoclaving (AC) cycle: the spectra are recorded at 20° C. (FIG. 2A, 2B) or 37° C. (FIG. 2C, 2D).

From FIG. 1A (or 1C) it is evident that the addition of the stabilizer (FA/emulsifier) to the reference solution containing HA+Vitamin E enhances the viscoelastic properties (both G', G") of the resulting solution.

After the AC treatment, the above difference becomes even larger: cf. FIG. 1A vs. 1B (or FIG. 1C vs. 1D) showing that, for the solution of the invention, the values G' and G" are highly preserved after the AC treatment, whereas in the reference solution they undergo a clear decline.

From FIG. 2A (or 2C) it is evident that the addition of the stabilizer (CD) to the reference solution containing HA+Vitamin E enhances the viscoelastic properties (both G', G") of the resulting solution.

After the AC treatment, the above difference becomes even larger: cf. FIG. 2A vs. 2B (or FIG. 2C vs. 2D) showing that, for the solution of the invention, the values G' and G" are highly preserved after the AC treatment, whereas in the reference solution they undergo a clear decline.

In the following table 2 the ratio of elastic modulus of Ex4 and Ex 2 respect to Ex5 at 1 Hz are reported. The data show that the addition of CD (or FA+emulsifier) to a reference solution of HA and Vitamin E leads to an increase of, at the least twice, the elastic modulus ratio. This result indicates that both CD or FA interact with vitamin E and HA through secondary bonds cooperating in the formation of complexes among the molecules that stabilize the network. These cooperating complexes are further stabilised (i.e. better protected) when the formulations are thermally processed by heating at a temperature between 80° C. and 130° C. for a processing time between 10 and 30' and then quickly cooled at 20/37° C. After the thermal treatment and the quenching there is an increase of the elastic modulus ratio that is from 4 to 12 times due to the presence of CD or FA+emulsifier.

TABLE 2

The elastic modulus ratio at 1 Hz of the examples formulations.

| Ratio | 20° C. | 20° C. after AC | 37° C. | 37° C. after AC |
|---|---|---|---|---|
| $G'_{Ex.2}/G'_{Ex.5}$ | 2 | 4 | 2.5 | 6 |
| $G'_{Ex.4}/G'_{Ex.5}$ | 2.1 | 6 | 2.3 | 12 |

3. Rheological Synergism of the Cooperating Complexes

The interactions between HA, VE, and CD or FA+emulsifier lead to cooperating complexes that stabilize the network and result in improved rheological properties. This improvement in the viscoelastic properties indicates that exists a rheological synergism between HA and Vit E and CD or HA and Vit E and FA. The rheological synergy can be quantified by the interaction parameter, that is the difference between the dynamic modulus values of the mixture evaluated by rheological test and the theoretical one given by adding the dynamic modulus values of the primary components. For the composition of Ex. 2 the synergistic parameter ($\Delta G'_{Synergistic}$) is described by the following formula (1), wherein a positive value of $\Delta G'_{Synergistic}$ indicates the presence of synergism.

$$\Delta G'_{Synergistic} = G'_{Ex.2} - (G'_{HA+VE} + G'_{FA}) \qquad (1)$$

The results of the calculation of synergistic parameters for Ex. 2 at 20 and 37° C. before and after AC are reported in table 3.

TABLE 3 the interaction parameters of Ex. 2 at 1 Hz

| Condition | $G'_{Ex.2}$ [Pa] | $G'_{HA+VE}$ [Pa] | $G'_{FA}$ [Pa] | $\Delta G'_{Synergistic}$ [Pa] | Synergism |
|---|---|---|---|---|---|
| 20° C. | 150 | 78 | 0.015 | +72 | YES |
| 20° C. After AC | 55 | 13 | 0.011 | +42 | YES |
| 37° C. | 133 | 53 | 0.015 | +80 | YES |
| 37° C. After AC | 49 | 8 | 0.011 | +41 | YES |

For the final composition of Ex. 4 the synergistic parameter $\Delta G'_{Synergistic}$ is described by formula (2) at 20 and 37° C. before and after AC:

$$\Delta G'_{Synergistic} = G'_{Ex.4} - (G'_{HA+VE} + G'_{CD}) \quad (2)$$

The results of the calculation of synergistic parameters for Ex. 4 at 20 and 37° C. before and after AC are reported in table 4.

TABLE 4 the interaction parameters of Ex. 4 at 1 Hz.

| Condition | $G'_{Ex.4}$ [Pa] | $G'_{HA+VE}$ [Pa] | $G'_{CD}$ [Pa] | $\Delta G'_{Synergistic}$ [Pa] | Synergism |
|---|---|---|---|---|---|
| 20° C. | 166 | 78 | 0.013 | +88 | YES |
| 20° C. After AC | 78 | 13 | 0.011 | +65 | YES |
| 37° C. | 130 | 53 | 0.013 | +77 | YES |
| 37° C. After AC | 48 | 8 | 0.013 | +40 | YES |

The data in table 3 (Ex. 2) and table 4 (Ex. 4) show a strongly positive ($\Delta G'_{Synergistic}$) parameter, thus indicating a strong synergism. This remains well evident for the solutions measured at different temperature (20 or 37° C.), either prior or after the autoclaving cycle.

4. Mechanical Stability of the Formulations

Figure 3:
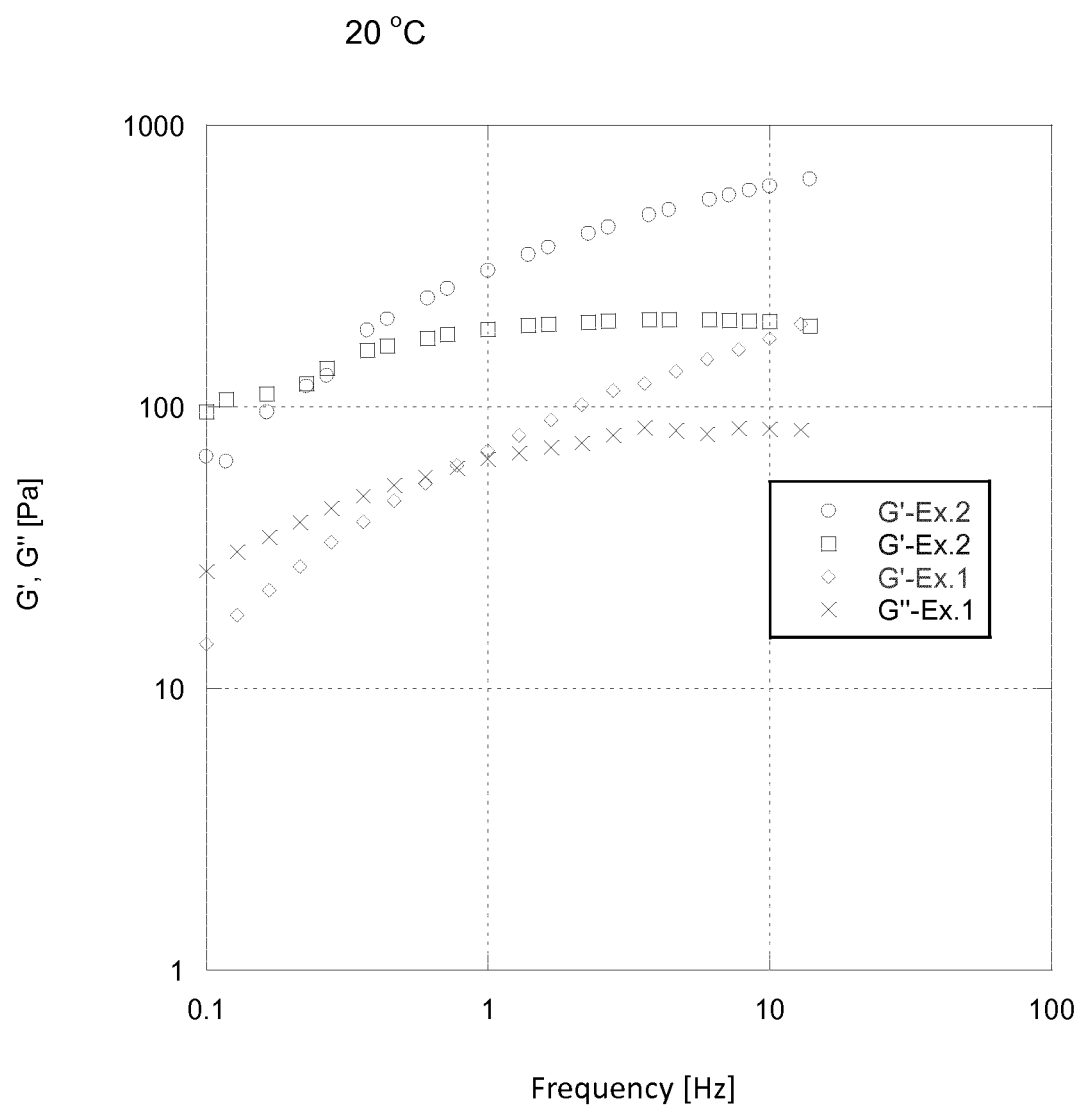
FIG. 3 compares the mechanical spectra of Example 2 (invention) and 1 (reference), recorded prior/after performing the autoclaving (AC) cycle: the spectra are recorded at 20° C.
Figure 3:
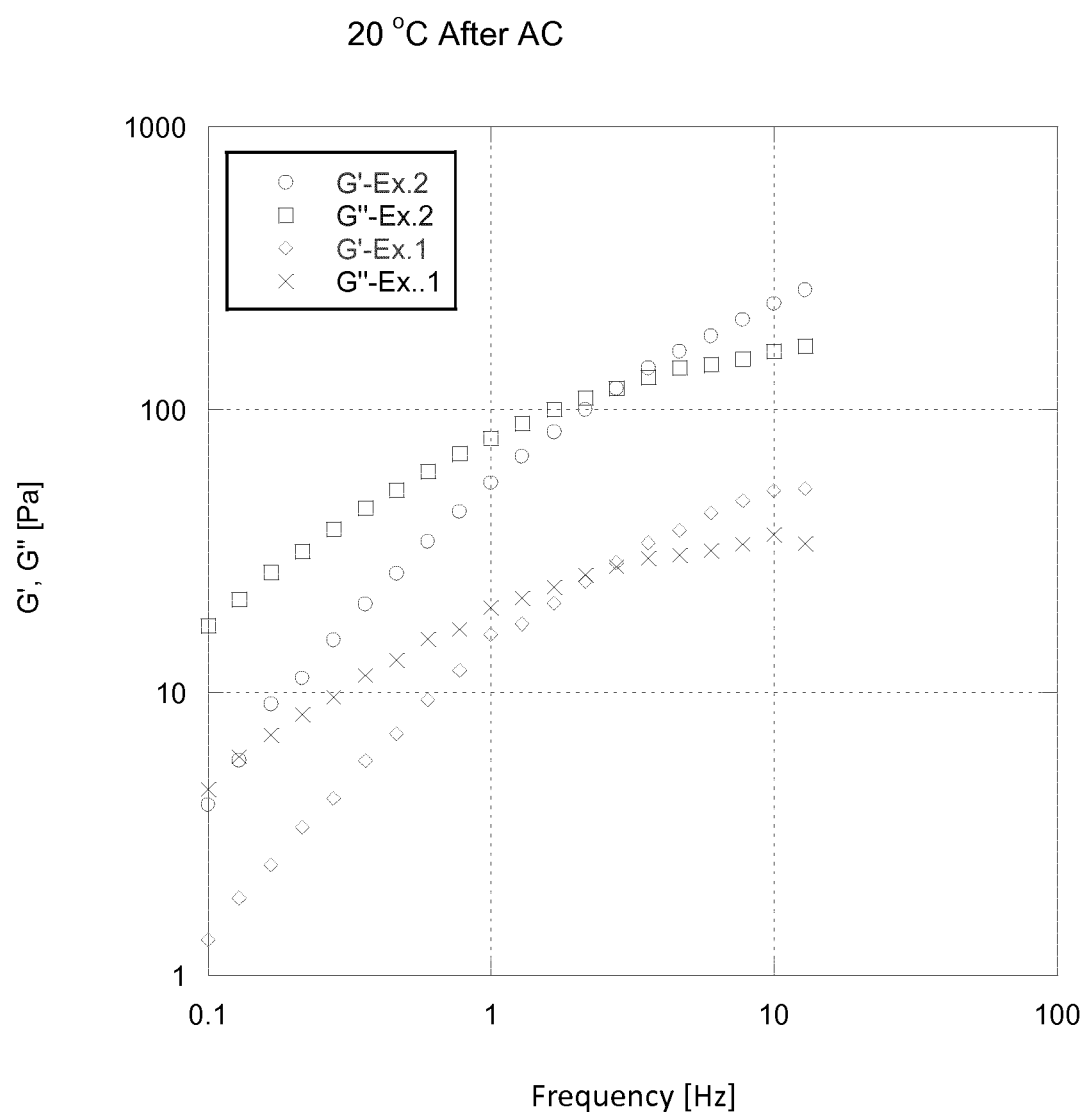
Figure 3:
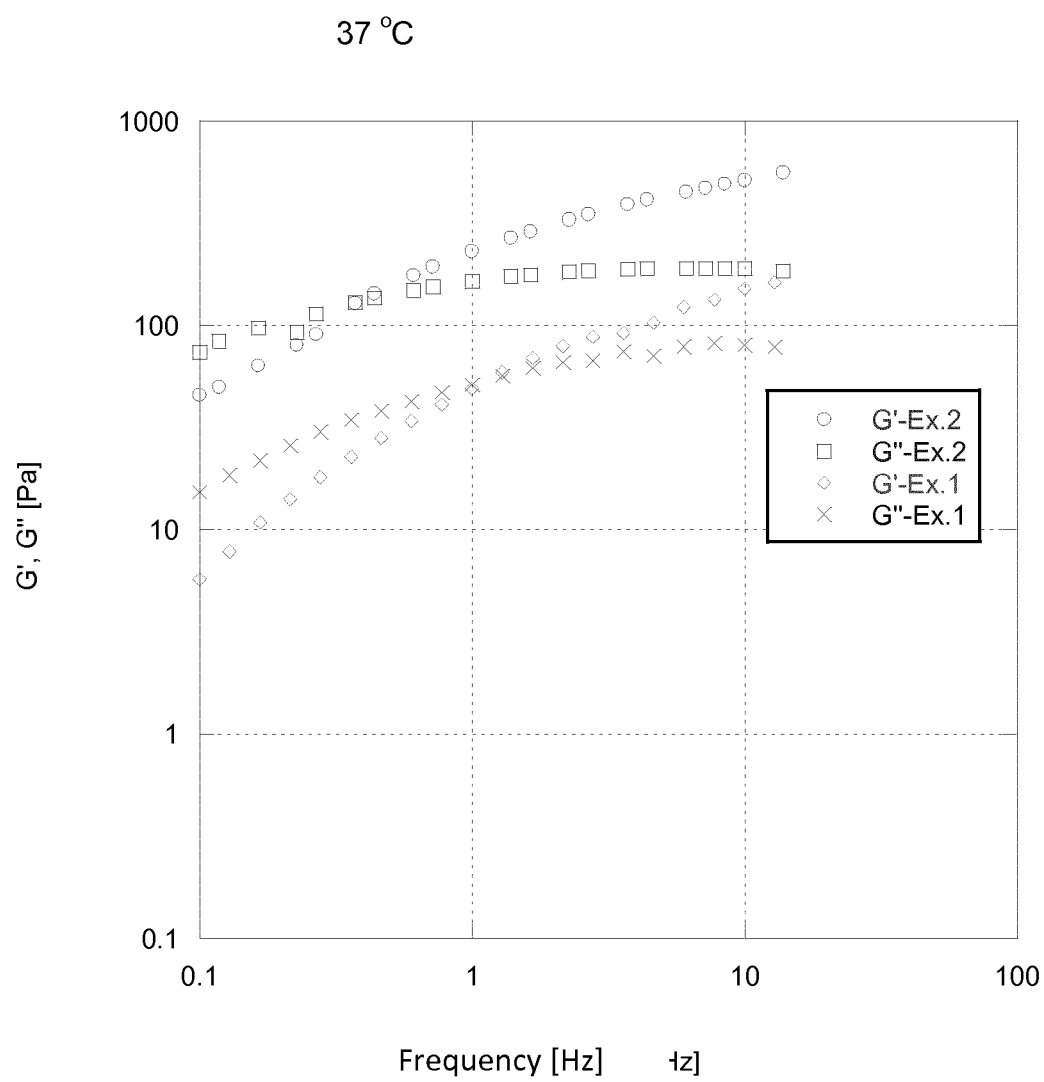
Figure 3:
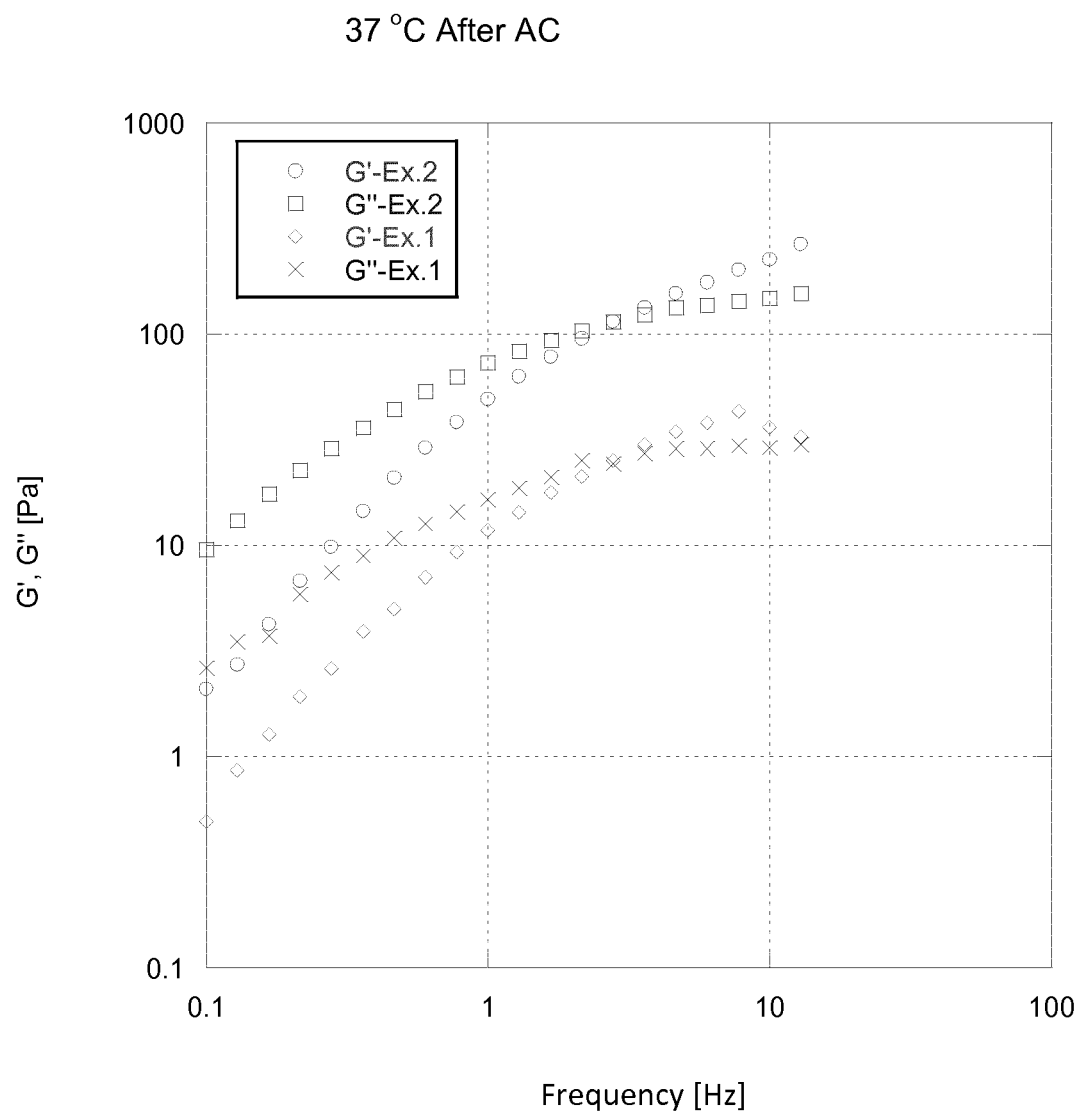
Figure 4:
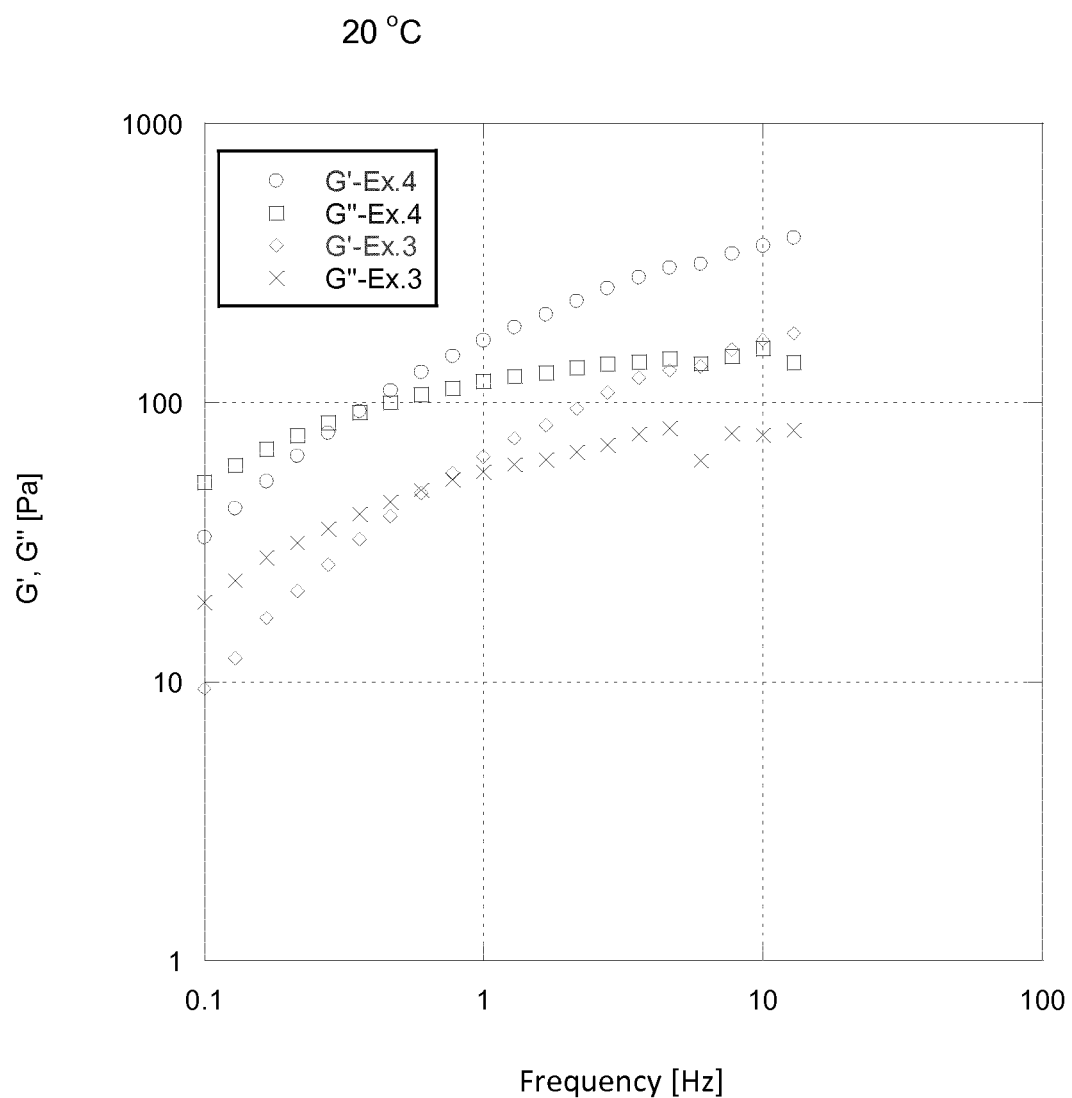
FIG. 4 compares the mechanical spectra of Example 4 (invention) and 3 (reference), recorded prior/after performing the autoclaving (AC) cycle: the spectra are recorded at 20° C.
Figure 4:
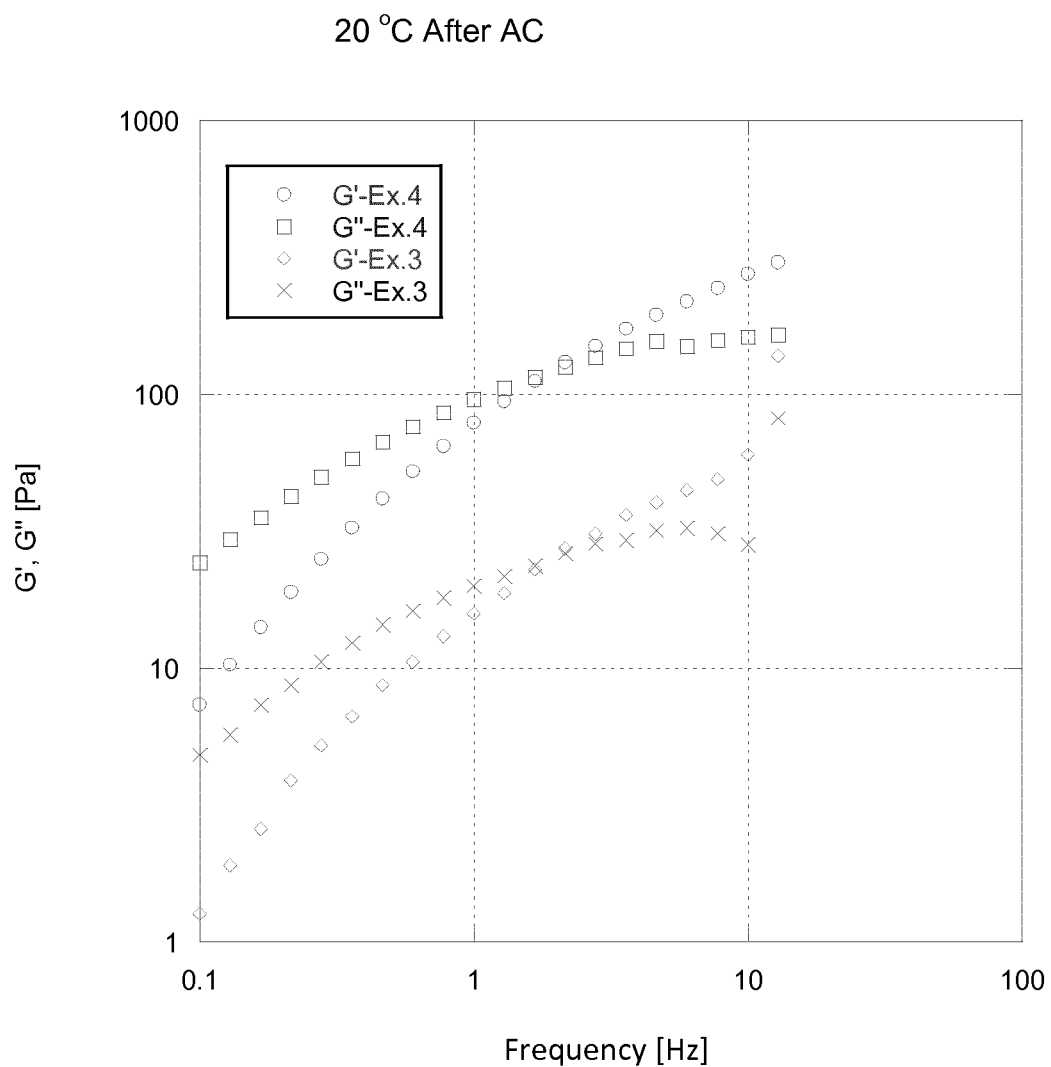
Figure 4:
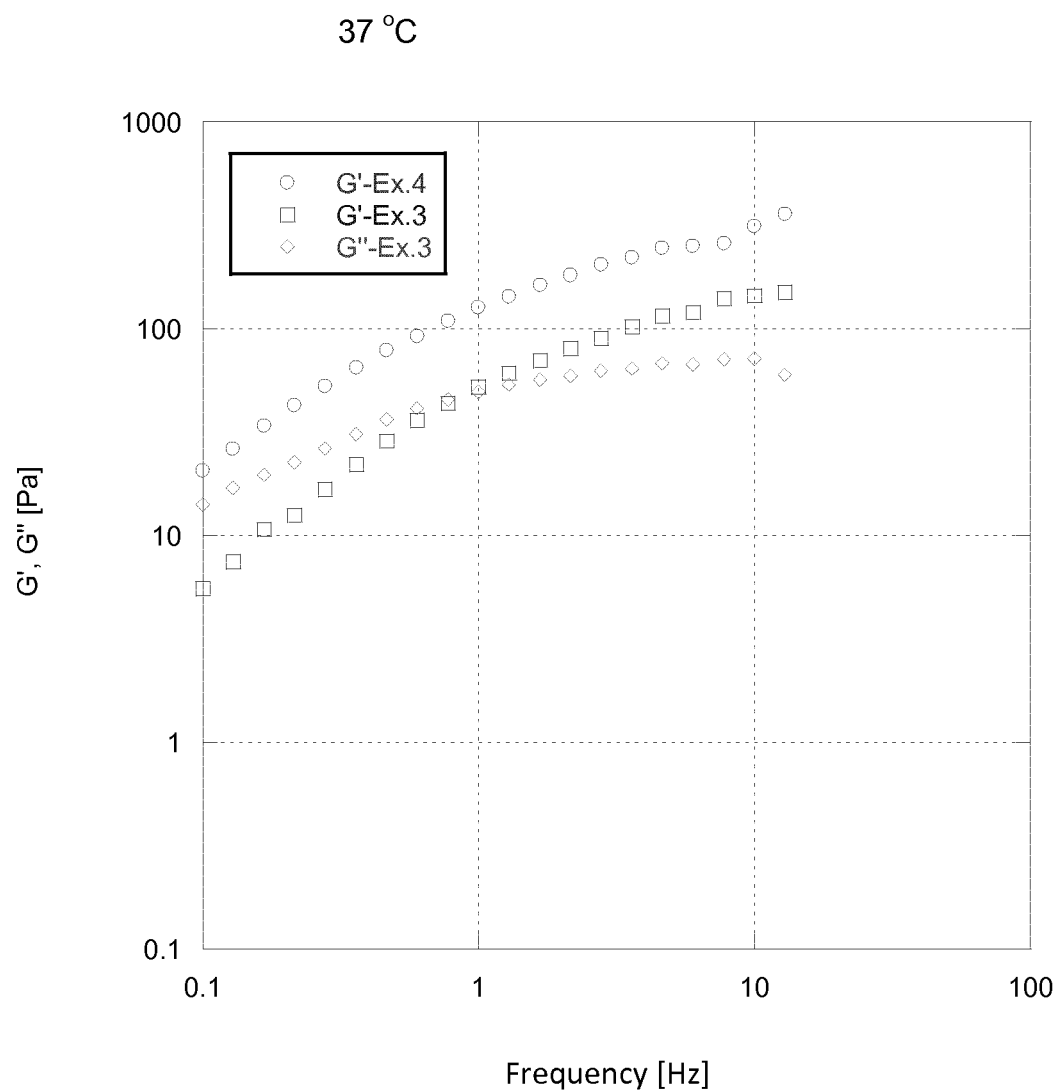
Figure 4:
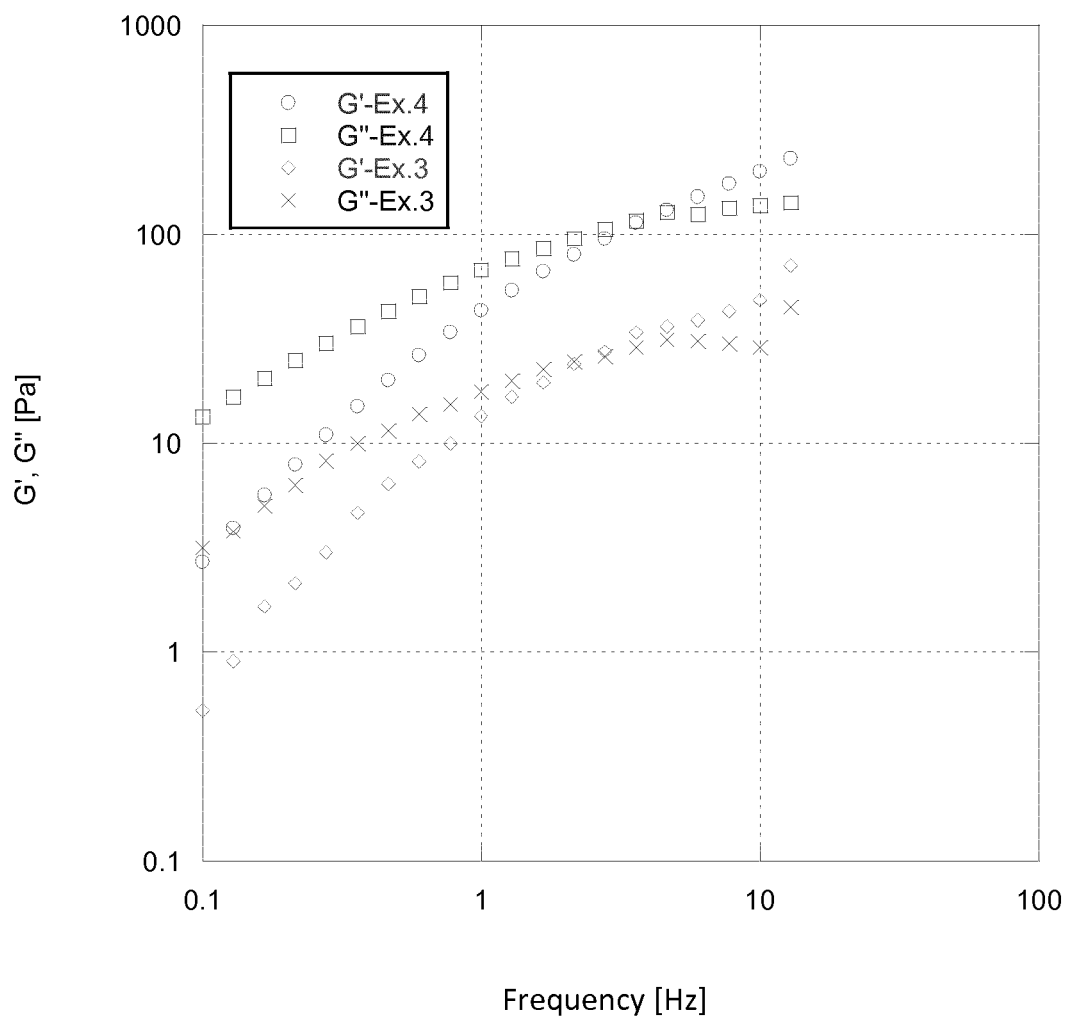

The comparison between the mechanical spectra of Ex. 1 and Ex. 2 as well as Ex. 3 and Ex. 4 are shown in FIGS. 3 and 4, respectively. In particular:

FIG. 3 compares the mechanical spectra of Example 2 (invention) and 1 (reference), prior/after performing the autoclaving (AC) cycle: the spectra are recorded at 20° C. (FIG. 3A, 3B) or 37° C. (FIG. 3C, 3D).

FIG. 4 compares the mechanical spectra of Example 4 (invention) and 3 (reference), prior/after performing the autocalving (AC) cycle: the spectra are recorded at 20° C. (FIG. 4A, 4B) or 37° C. (FIG. 4C, 4D).

As it can be seen from FIG. 3A (or 3C), the addition of Vit E increased the stability of the Ex. 2 formulation in comparison with the reference Ex. 1 which does not possess Vit E. Moreover, the same trend is observable when the mechanical spectra of Ex. 4 is compared to Ex. 3 that does not have Vit E (FIG. 4). The presence of Vit E is thus essential for the formation of the cooperating complexes and for the stabilization of the network and the consequence improvement of the viscoelastic properties.

Tables 5 and 6 report the values of G' and G" for Ex. 1, Ex. 2 and Ex 3, Ex 4 respectively, at 20 and 37° C. before and after AC. As it can be from the tables, before autoclaving, G' of Ex 2 [150 Pa] and G' of Ex 4 [166 Pa] are more than two folds higher than G' Ex 1 and Ex 3. Furthermore, after the thermal processing the viscoelastic properties of the ternary systems are better preserved, indicating that the cooperating complexes that are created by the interactions among the HA and CD and Vit E or HA, Vit E and FA stabiles the network systems of these formulations. Indeed G' of Ex 2 after autoclaving tested at 37° C. is 49 Pa while G' of Ex 1 is 2 Pa and G' of Ex 4 is 43 Pa while G' of Ex 3 is 15 Pa.

TABLE 5

The values of G' and G" at 1 Hz for formulations of Ex. 1 and Ex. 2.

| | Before AC at 20° C. | | After AC at 20° C. | | Before AC at 37° C. | | After AC at 37° C. | |
|---|---|---|---|---|---|---|---|---|
| Entry | G' [Pa] | G" [Pa] | G' [Pa] | G" [Pa] | G' [Pa] | G" [Pa] | G' [Pa] | G" [Pa] |
| Example 1 (reference) | 72 | 63 | 15 | 20 | 49 | 51 | 2 | 11 |
| Example 2 (invention) | 150 | 107 | 55 | 80 | 133 | 100 | 49 | 72 |

TABLE 6

The values of G' and G" at 1 Hz for formulations of Ex. 3 and Ex. 4.

| | Before AC at 20 | | After AC at 20 | | Before AC at 37 | | After AC at 37 | |
|---|---|---|---|---|---|---|---|---|
| Entry | G' [Pa] | G" [Pa] | G' [Pa] | G" [Pa] | G' [Pa] | G" [Pa] | G' [Pa] | G" [Pa] |
| Example 3 (reference) | 66 | 57 | 17 | 24 | 53 | 49 | 15 | 20 |
| Example 4 (invention) | 166 | 119 | 78 | 98 | 126 | 98 | 43 | 67 |

The table 5 further shows a better viscoelastic performance for the example 2 of the invention, compared to example 1; the higher viscoelastic performance of Example 2 remains also after the AC, showing a better protection of viscoelastic properties compared to the Example 1.

The table 6 further shows a better viscoelastic performance for the example 4 of the invention, compared to example 3; the higher viscoelastic performance of Example 4 remains also after the AC, showing a better protection of viscoelastic properties compared to the Example 3.

5. Drug Solubility of the Formulations

Different amounts of DF-Na including 2.5, 5.7, and 20 mg/ml were added to the formulation of Example 4, the formulations were stirred until being completely homogenised. Once prepared they were kept for 24 hrs and after centrifuged (6000 rpm for 15 min). Finally, the supernatants were analyzed by means of UV spectrophotometer. The tests were performed in triplicate and the wavelengths used for the detection of diclofenac sodium was 276 nm. In order to associate the recorded absorbance to the amount of DF-Na in the supernatant, a calibration curve was constructed by plotting absorbance against predetermined concentration of DF-Na. Then, linear regression was used to determine the regression equation representing the calibration curve. The results of the dissolution tests are reported in table as solubilized fraction (SF) as the ratio between DF-Na which was found into the supernatant of the solution, and total DF-Na as expressed by:

$$SF\% = \frac{\text{solubilized } DF}{\text{Total } DF} \times 100$$

The results of dissolution test are shown in table 7.

TABLE 7

Solubilized fraction (SF) of Ex. 4 with different concentration of DF-Na

| Total DF-Na, mg/ml | Solubilized fraction (SF), % |
| --- | --- |
| 2.5 | 93 |
| 5.7 | 89 |
| 20 | 78 |

6. Drug Release Ability of the Formulations

Figure 5:
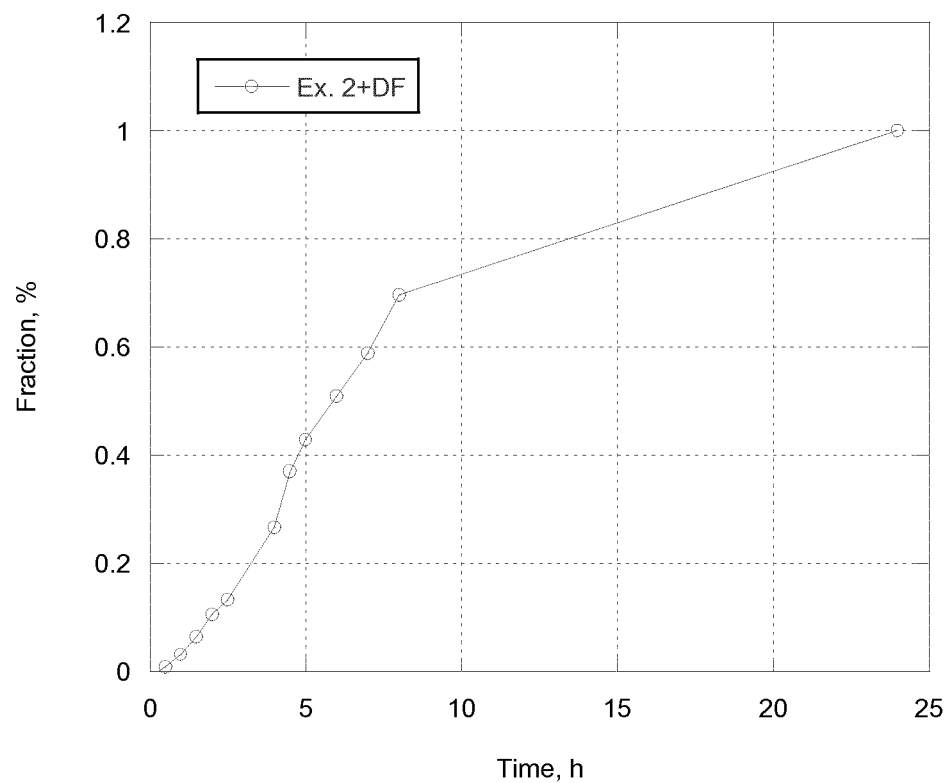
FIG. 5 The drug release kinetic of Ex. 2 (A) and Ex. 4 (B) loaded with Diclofenac sodium (DF-Na).
Figure 5:
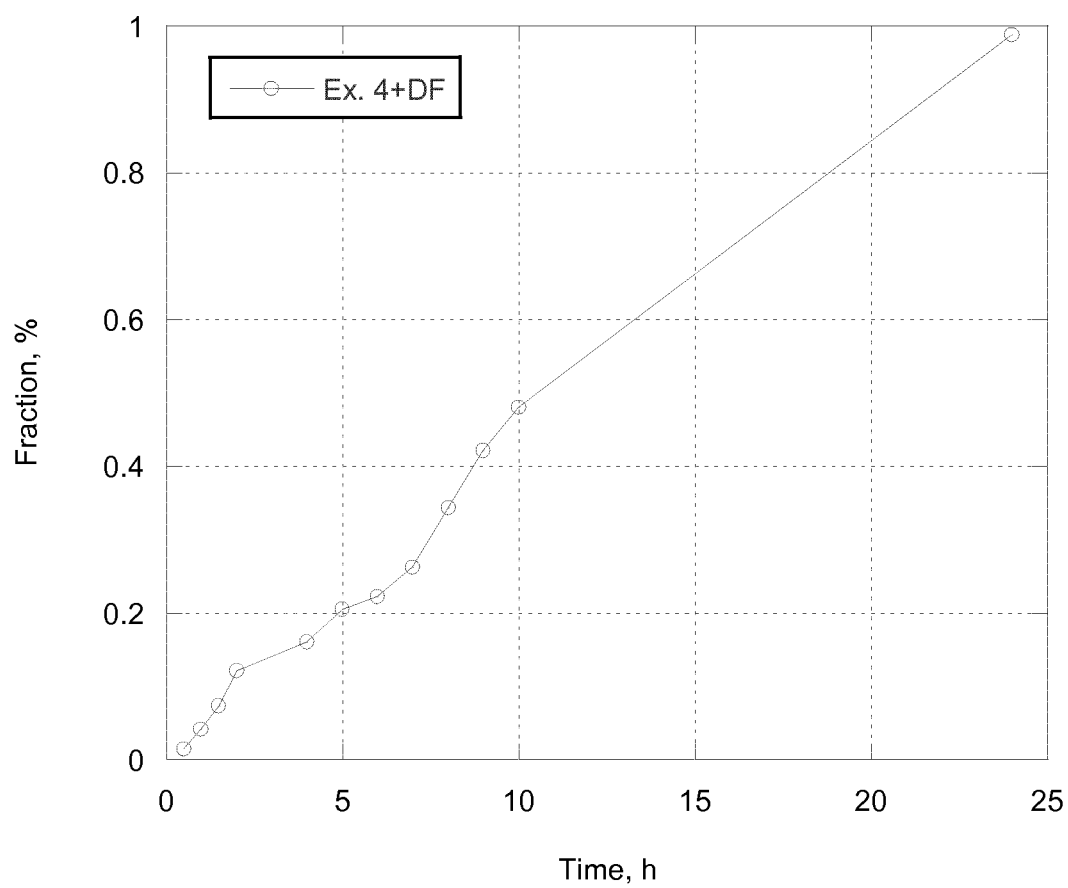

The drug release profiles from the formulation of Ex 2 and Ex 4 loaded with diclofenac sodium (DF-Na) are shown in FIG. 5. To perform the release test, 1 gr of the formulation containing DF-Na at 1% was inserted in a dialysis membrane, with cut off 500 to 1000 Da, that was immersed in PBS medium (18 ml) at the temperature of 37° C. At predetermined time intervals, 50 μL aliquots of the medium was withdrawn and the same volume of fresh medium was added. The drug concentration released into the PBS buffer was detected by UV spectrophotometer as a function of time. The calibration curve was constructed as explained in the previous paragraph. The tests were performed in triplicate and the wavelengths used for the detection of diclofenac sodium was 276 nm.

For the formulation of Ex. 2 with DF-Na (FIG. 5 A), it can be seen that after 8 hours 69% of the drug was released in the medium and after 24 hrs there is the complete release of the drug. Moreover, for the Ex. 4 with DF-Na (FIG. 5 B), it can be seen that after 10 hours 48% of the drug was released in the medium and after 24 hrs there is the complete release of the drug. These formulations are able to control the delivery of the drug molecules over the time. There was very good reproducibility between the triplicates. Prominently, no significant differences between samples was observed which indicate a homogenous diffusion in the prepared composition.

The invention claimed is:

1. A synergistically cooperative, aqueous solution comprising components in dissolved form:
   (a) hyaluronic acid or a salt thereof at a weight concentration of 0.01 to 25%,
   (b) a cyclodextrin at a weight concentration of 0.01 to 25%,
   (c) one or more tocopherols or tocotrienols and mixtures thereof at a weight concentration of 0.0001 to 15%, by weight of the solution,
   wherein said components (a), (b) and (c) are not engaged in formal chemical binding with each other, and
   wherein the synergistically cooperative, aqueous solution with the components in dissolved form exhibits an increased dynamic modulus (G') from said components (a), (b) and (c) over an added, dynamic modulus (G') calculated from said components (a), (b) and (c).

2. The solution according to claim 1, wherein the hyaluronic acid is in form of two or more fractions thereof with different average molecular weights, each between 40 to 4000 kDa.

3. The solution according to claim 1, wherein the hyaluronic acid salt is selected from the group consisting of sodium, potassium, ammonium, calcium, magnesium, zinc and cobalt salts and mixtures thereof.

4. The solution according to claim 1, wherein the cyclodextrin is selected from the group consisting of: α-cyclodextrin, β-cyclodextrin, γ-cyclodextrin, propyl-β-cyclodextrin, hydroxypropyl-β-cyclodextrin, hydroxypropyl-γ-cyclodextrin, sulfobutyl-β-cyclodextrin, sulfobutyl ether 4-beta-cyclodextrin, amino or hydrazino-β-cyclodextrin and mixtures thereof.

5. The solution according to claim 1, wherein the tocopherol is chosen from the group consisting of an α-, β-, γ- or δ-tocopherol and mixtures thereof.

6. The solution according to claim 1, wherein the tocotrienol is chosen from the group consisting of an α-, β-, γ- and δ-tocotrienol and mixtures thereof.

7. The solution according to claim 1, further comprising a pharmaceutically- or cosmetically active agent.

8. The solution according to claim 7, wherein the pharmaceutically active agent includes one or more non-steroidal anti-inflammatory drugs.

9. The solution according to claim 8, wherein the anti-inflammatory drug is selected from the group consisting of salicylic acid, aspirin, mefenamic acid, tolfenamic acid, flufenamic acid, diclofenac, sulindac, fenbufen, indometacin, acemetacin, amfenac, etodolac, felbinac, ibuprofen, flurbiprofen, ketoprofen, naproxen, pranoprofen, fenoprofen, tiaprofenic acid, oxaprozin, loxoprofen, alminoprofen, zaltoprofen, piroxicam, tenoxicam, lornoxicam, meloxicam, tiaramide, tolmetin, diflunisal, acetaminophen, floctafenine, tinoridine, actarit, pharmaceutically acceptable salts thereof and mixtures thereof, in concentration of 0.0001 to 10% by weight of the solution.

10. The solution according to claim 9, wherein the anti-inflammatory drug is diclofenac sodium.

11. A process of preparing a synergistically cooperative, aqueous solution according to claim 1, comprising forming an aqueous solution of a hyaluronic acid or a salt thereof at a weight concentration of 0.01 to 25%, a cyclodextrin at a weight concentration of 0.01 to 25% by weight and one or more tocopherols or tocotrienols and mixtures thereof at a weight concentration of 0.0001 to 15%, by weight of the solution.

12. A method of treatment selected from: dermo-cosmetic method, esthetic method, soft tissue augmentation method, viscosupplementation method, dermal-filling method, and regenerative method, comprising administering the solution according to claim 1 to a patient in need thereof.

13. The solution according to claim 1, wherein the weight concentration of the hyaluronic acid or a salt thereof is 2 to 25%, the weight concentration of the cyclodextrin is 2 to 25%, and the weight concentration of the one or more tocopherols or tocotrienols and mixtures thereof is 2 to 25%.

14. The process of preparing a solution according to claim 11, wherein the weight concentration of the hyaluronic acid or a salt thereof is 2 to 25%, the weight concentration of the cyclodextrin is 2 to 25%, and the weight concentration of the one or more tocopherols or tocotrienols and mixtures thereof is 2 to 25%.

\* \* \* \* \*